United States Patent
Sommers et al.

(10) Patent No.: US 11,033,433 B2
(45) Date of Patent: Jun. 15, 2021

(54) REMOVABLE SHIELD FOR PROTECTIVE HEADWEAR

(71) Applicant: Illinois Tool Works Inc., Glenview, IL (US)

(72) Inventors: Eric T. Sommers, Appleton, WI (US); Nishank R. Patel, Appleton, WI (US); Samuel B. Petre, Wauwatosa, WI (US); John C. Mehnert, Madison, WI (US)

(73) Assignee: ILLINOIS TOOL WORKS INC, Glenview, IL (US)

( * ) Notice: Subject to any disclaimer, the term of this patent is extended or adjusted under 35 U.S.C. 154(b) by 0 days.

(21) Appl. No.: 14/737,022

(22) Filed: Jun. 11, 2015

(65) Prior Publication Data

US 2015/0359679 A1     Dec. 17, 2015

Related U.S. Application Data

(60) Provisional application No. 62/012,497, filed on Jun. 16, 2014.

(51) Int. Cl.
*A61F 9/06* (2006.01)
*A42B 3/22* (2006.01)

(52) U.S. Cl.
CPC .............. *A61F 9/064* (2013.01); *A42B 3/225* (2013.01)

(58) Field of Classification Search
CPC .......... A61F 9/064; A61F 9/061; A61F 9/062; A61F 9/06; A42B 3/225; A42B 3/22; A42B 3/221; A42B 3/222; A42B 3/223; A42B 3/224; A42B 3/226; A42B 3/227; A42B 3/228; A42B 3/18; A42B 3/20
(Continued)

(56) References Cited

U.S. PATENT DOCUMENTS 1,182,367 A    5/1916 Gravell
1,338,022 A    4/1920 Lamoreaux
(Continued)

FOREIGN PATENT DOCUMENTS

CN    101056677 A    10/2007
CN    101795645 A    8/2010
(Continued)

OTHER PUBLICATIONS

International Search Report and Written Opinion for PCT/US2015/033054 dated Aug. 31, 2015, 12 pages.
(Continued)

*Primary Examiner* — Jameson D Collier
*Assistant Examiner* — F Griffin Hall
(74) *Attorney, Agent, or Firm* — Klintworth & Rozenblat IP LLP

(57) ABSTRACT

In one aspect, a protective headwear is provided and includes a headgear, an outer shell rotatably coupled to the headgear, and a first shield coupled to the outer shell and rotatable between a first position and a second position. The first shield is selectively removable from the outer shell without the use of tools. The protective headwear also includes a second shield coupled to the outer shell. The first shield covers the second shield to a greater extent in the first position than in the second position. In one aspect, a method of manufacturing a protective headwear is provided.

21 Claims, 18 Drawing Sheets

(58) Field of Classification Search
USPC ...... 2/8.5, 8.1, 8.2, 6.4, 7, 6.1, 6.2, 6.3, 6.5, 2/8.3
See application file for complete search history.

(56) References Cited

U.S. PATENT DOCUMENTS

| | | | |
|---|---|---|---|
| 1,601,830 A | 10/1926 | Huntsman | |
| 1,994,103 A | 3/1935 | Huey | |
| 2,169,745 A | 8/1939 | Shipman | |
| 2,194,492 A | 3/1940 | Bowers | |
| 2,402,820 A | 6/1946 | Kitchen | |
| 2,411,831 A | 11/1946 | Lehmberg et al. | |
| 2,487,848 A | 11/1949 | Bowers | |
| 2,658,200 A | 11/1953 | Bowers, Sr. | |
| 2,700,158 A | 1/1955 | Larsen | |
| 2,763,006 A | 9/1956 | Amundsen | |
| 3,074,072 A | 1/1963 | Edwards et al. | |
| 3,112,745 A | 12/1963 | Boyer | |
| 3,119,279 A | 1/1964 | Reece | |
| 3,214,768 A | 11/1965 | Bohner | |
| 3,413,972 A | 12/1968 | Depping | |
| 3,430,263 A | 3/1969 | Newcomb | |
| 3,584,314 A | 6/1971 | Hobson | |
| 3,609,765 A | 10/1971 | Molitoris | |
| 3,696,442 A | 10/1972 | Amundsen | |
| 3,868,727 A | 3/1975 | Paschall | |
| 3,881,478 A | 5/1975 | Rosendahl | |
| 3,914,796 A | 10/1975 | Barta | |
| 3,955,570 A | 5/1976 | Hutter, III | |
| 4,011,865 A | 3/1977 | Morishita | |
| 4,040,123 A | 8/1977 | Williams | |
| 4,080,664 A | 3/1978 | Morris et al. | |
| 4,109,320 A | 8/1978 | Anderson | |
| 4,293,757 A | 10/1981 | Niemi | |
| 4,335,472 A | 6/1982 | Rappleyea | |
| D270,642 S | 9/1983 | Watts | |
| 4,464,800 A | 8/1984 | Edwards | |
| 4,479,738 A | 10/1984 | Kubnick | |
| 4,499,630 A | 2/1985 | Harris | |
| 4,793,001 A | 12/1988 | Accardi | |
| 4,853,973 A * | 8/1989 | Boochard | A61F 9/06 2/8.1 |
| 5,003,632 A | 4/1991 | Claude | |
| 5,012,528 A | 5/1991 | Pernicka | |
| 5,044,019 A | 9/1991 | Shewchenko | |
| 5,077,836 A | 1/1992 | Idoff et al. | |
| 5,386,592 A | 2/1995 | Checkeroski | |
| 5,412,811 A | 5/1995 | Hildenbrand | |
| 5,724,119 A | 3/1998 | Leight | |
| D393,933 S | 4/1998 | Huh | |
| 5,752,280 A | 5/1998 | Hill | |
| D398,421 S | 9/1998 | Crafoord | |
| 6,032,297 A | 3/2000 | Barthold et al. | |
| 6,035,451 A * | 3/2000 | Burns | A42B 3/10 2/424 |
| 6,102,033 A * | 8/2000 | Baribeau | A62B 18/08 128/201.24 |
| 6,154,881 A | 12/2000 | Lee | |
| 6,185,739 B1 | 2/2001 | Verkic et al. | |
| 6,260,197 B1 | 7/2001 | Hoogewind | |
| 6,264,392 B1 | 7/2001 | Wise | |
| 6,298,498 B1 | 10/2001 | Burns et al. | |
| 6,341,382 B1 | 1/2002 | Ryvin et al. | |
| 6,367,085 B1 | 4/2002 | Berg | |
| 6,393,617 B1 | 5/2002 | Paris | |
| D467,489 S | 12/2002 | Rubinson | |
| D489,492 S | 5/2004 | Wu | |
| 6,782,558 B1 | 8/2004 | Keen, Sr. et al. | |
| 6,973,672 B2 * | 12/2005 | Huh | A61F 9/067 2/8.1 |
| 6,973,676 B1 | 12/2005 | Simpson | |
| D521,190 S | 5/2006 | Wu | |
| 7,089,603 B2 | 8/2006 | Ketterer et al. | |
| D530,185 S | 10/2006 | Osiecki | |
| 7,120,939 B1 | 10/2006 | Howard | |
| 7,178,932 B1 | 2/2007 | Buckman | |
| 7,284,281 B2 * | 10/2007 | Huh | A61F 9/06 2/8.2 |
| D557,128 S | 12/2007 | Sawdon | |
| 7,308,719 B2 * | 12/2007 | Huh | A61F 9/065 2/8.2 |
| 7,318,437 B2 | 1/2008 | Gunaratnam | |
| 7,441,282 B2 | 10/2008 | Heine | |
| D584,003 S | 12/2008 | Juhlin | |
| D589,654 S | 3/2009 | Juhlin | |
| 7,534,005 B1 | 5/2009 | Buckman | |
| D602,639 S | 10/2009 | Ho | |
| D635,721 S | 4/2011 | Cheng | |
| 8,056,152 B2 | 11/2011 | Brace | |
| D654,224 S | 2/2012 | Wu | |
| D654,634 S | 2/2012 | Wu | |
| 8,214,920 B1 | 7/2012 | Edgar | |
| D667,173 S | 9/2012 | Juhlin et al. | |
| 3,286,269 A1 | 10/2012 | Springer et al. | |
| 8,336,114 B1 | 12/2012 | Lee | |
| D674,150 S | 1/2013 | Juhlin et al. | |
| D674,153 S | 1/2013 | Daniels et al. | |
| 8,381,312 B2 * | 2/2013 | Seo | A61F 9/064 2/8.4 |
| 8,387,162 B2 | 3/2013 | Huh | |
| 8,584,265 B2 | 11/2013 | Lilenthal et al. | |
| 8,627,517 B2 | 1/2014 | Ahlgren et al. | |
| D710,546 S | 8/2014 | Wu | |
| 8,826,464 B2 | 9/2014 | Wu | |
| 8,990,963 B2 | 3/2015 | Matthews | |
| 9,038,198 B2 * | 5/2015 | Feinberg | G02B 7/006 2/8.2 |
| D735,949 S | 8/2015 | Dion | |
| D735,951 S | 8/2015 | Birath | |
| 9,155,923 B2 | 10/2015 | Proctor | |
| D742,596 S | 11/2015 | Peng | |
| D743,629 S | 11/2015 | Peng | |
| D747,556 S | 1/2016 | Fujita | |
| D749,796 S | 2/2016 | Barmore | |
| 9,427,040 B2 | 8/2016 | Leyland | |
| D767,829 S | 9/2016 | Wu | |
| 9,706,805 B2 | 7/2017 | Pereira | |
| 9,956,118 B2 * | 5/2018 | Sernfalt | A61F 9/06 |
| 2003/0135911 A1 * | 7/2003 | Wang-Lee | A61F 9/064 2/169 |
| 2004/0179149 A1 * | 9/2004 | Wang-Lee | A61F 9/061 349/58 |
| 2006/0080761 A1 | 4/2006 | Huh | |
| 2006/0225187 A1 | 10/2006 | Wu | |
| 2007/0050892 A1 | 3/2007 | Charles | |
| 2007/0113318 A1 | 5/2007 | Weston | |
| 2007/0220649 A1 * | 9/2007 | Huh | A61F 9/025 2/9 |
| 2007/0245467 A1 | 10/2007 | Lilenthal | |
| 2008/0060102 A1 | 3/2008 | Matthews | |
| 2009/0089908 A1 | 4/2009 | Huh | |
| 2009/0210989 A1 | 8/2009 | Becker et al. | |
| 2009/0235420 A1 * | 9/2009 | Chiang | A61F 9/06 2/8.5 |
| 2010/0050325 A1 | 3/2010 | Wang-Lee | |
| 2010/0212058 A1 * | 8/2010 | Wanhainen | A42B 3/225 2/8.2 |
| 2010/0229274 A1 | 9/2010 | Ahlgren | |
| 2010/0229286 A1 | 9/2010 | Ahlgren | |
| 2010/0235971 A1 | 9/2010 | Ahlgren | |
| 2010/0287676 A1 | 11/2010 | Seo | |
| 2010/0294270 A1 | 11/2010 | Curran | |
| 2011/0101890 A1 * | 5/2011 | Robinson | F21V 21/084 315/320 |
| 2011/0167542 A1 | 7/2011 | Bayne | |
| 2011/0179541 A1 | 7/2011 | Wright | |
| 2011/0219506 A1 | 9/2011 | Uttrachi | |
| 2011/0265790 A1 | 11/2011 | Walker et al. | |
| 2012/0144565 A1 | 6/2012 | Huh | |
| 2012/0291172 A1 * | 11/2012 | Wills | B23K 9/0956 2/8.2 |
| 2013/0111653 A1 | 5/2013 | Huh | |
| 2013/0152919 A1 | 6/2013 | Billingsley et al. | |

(56) References Cited

U.S. PATENT DOCUMENTS

| | | | | |
|---|---|---|---|---|
| 2014/0007312 | A1* | 1/2014 | Wright | A61F 9/064 2/8.2 |
| 2014/0208476 | A1* | 7/2014 | Chen | A61F 9/064 2/8.7 |
| 2014/0298557 | A1* | 10/2014 | Townsend, Jr. | A61F 9/06 2/8.2 |
| 2015/0143669 | A1 | 5/2015 | Pereira et al. | |
| 2015/0264992 | A1* | 9/2015 | Happel | A42B 3/04 2/422 |
| 2015/0359680 | A1* | 12/2015 | Gardner | A61F 9/068 2/8.6 |
| 2016/0081856 | A1 | 3/2016 | Hofer-Kraner | |
| 2016/0183622 | A1* | 6/2016 | Patel | A42B 3/222 2/424 |
| 2016/0360821 | A1* | 12/2016 | Benton | A42B 3/06 |
| 2017/0112226 | A1* | 4/2017 | Watkins | A61F 9/064 |

FOREIGN PATENT DOCUMENTS

| | | | |
|---|---|---|---|
| CN | 101815556 | A | 8/2010 |
| CN | 101827538 | A | 9/2010 |
| CN | 102370541 | A | 3/2012 |
| CN | 102525731 | A | 7/2012 |
| CN | 102551956 | A | 7/2012 |
| CN | 103221005 | A | 7/2013 |
| CN | 203264074 | U | 11/2013 |
| EP | 2 184 039 | A1 | 5/2010 |
| EP | 2 462 825 | A2 | 6/2012 |
| EP | 2 462 826 | A2 | 6/2012 |
| EP | 2 907 401 | A1 | 8/2015 |
| WO | 2008/025083 | A1 | 3/2008 |
| WO | 2009/048829 | A1 | 4/2009 |
| WO | 2009/048836 | A1 | 4/2009 |
| WO | 2014160149 | A2 | 10/2014 |
| WO | 2015195495 | A1 | 12/2015 |

OTHER PUBLICATIONS

International Search Report and Written Opinion for PCT/US2015/035714 dated Oct. 8, 2015, 11 pages.

International Search Report and Written Opinion for PCT/US2015/065213 dated Mar. 16, 2016, 13 pages.

nyopools.com, How to set up the zodiac T5 suction cleaner through your skimmer, https://webarchive.org/web/20130627095500/http://www.inyopools.com/HowToPage/How-to-set-up-the-zodiac0t5-cleaner-through-your-skimmer.aspx, Jun. 27, 2013, Retreived via Wayback Machine on Apr. 19, 2016.

International Search Report and Written Opinion for PCT/US2015/035713 dated Oct. 27, 2015, 17 pages.

Office Action issued for EP 15 732 143.1-1017 dated Aug. 30, 2018, 5 pages.

Communication pursuant to Rule 94(3) EPC issued for EP 15 7 2 8 713.7 dated Jul. 11, 2018, 5 pages.

\* cited by examiner

REMOVABLE SHIELD FOR PROTECTIVE HEADWEAR

RELATED APPLICATIONS

The present application claims the priority benefit of co-pending U.S. Provisional Patent Application Ser. No. 62/012,497, filed Jun. 16, 2014, which is incorporated by reference herein.

FIELD OF THE INVENTION

The present disclosure generally relates to protective headwear and, more particularly, to shields for protective headwear.

BACKGROUND

Welding helmets are one type of protective headwear and some conventional welding helmets include a grinding shield to cover a wearer's eyes and a welding shield that covers the grinding shield. The wearer of the welding helmet views through both the grinding shield and the welding shield while performing a welding process. Welding shields are usually tinted or darkened in order to inhibit damage to the wearer's eyes while performing welding processes, whereas grinding shields are usually transparent and lack darkening characteristics or other features that inhibit viewing through the grinding shield. In some conventional welding helmets, the welding shield may be rotated to a position where it does not cover the grinding shield, but remains coupled to the welding helmet. This enables a wearer to view through only the grinding shield. This may be beneficial if the wearer is performing processes other than welding. During all movements and at all positions of the welding shield, the welding shield remains coupled to the welding helmet.

Welding shields can have a significant amount of weight due to the technology involved in the welding shield (e.g., self-darkening features). Moving the welding shield to another location on the welding helmet will alter the welding helmet's center of gravity and may cause the welding helmet to become unstable, shift from an ideal position to a less ideal position on the wearer's head, and/or apply pressure to the wearer's head and neck in a less than ideal manner. Furthermore, while the welding shield has been moved from the line of sight of the wearer and is not in use, the weight associated with the welding shield remains with the welding helmet.

SUMMARY

Thus, a need exists for protective headwear that resolves one or more of these deficiencies.

In one aspect, it is desirable to have protective headwear that is comfortable, stable, and minimizes the amount of weight or pressure applied to a wearer.

In one aspect, a welding helmet is provided and includes an outer shell and a welding shield selectively removable from the outer shell.

In one aspect, a welding helmet is provided and includes an outer shell and a welding shield selectively removable from the outer shell without the use of tools.

In one aspect, a welding helmet is provided and includes an outer shell and a welding shield rotatable relative to the outer shell and removable from the outer shell.

In one aspect, a protective headwear is provided and includes a headgear, an outer shell rotatably coupled to the headgear, a first shield and a second shield. The first shield is coupled to the outer shell and is rotatable between a first position and a second position. The first shield is selectively removable from the outer shell without the use of tools. The second shield is coupled to the outer shell and the first shield covers the second shield to a greater extent in the first position than in the second position.

In one aspect, the outer shell may rotate relative to the headgear and the first shield may rotate relative to the outer shell about a same axis.

In one aspect, the protective headwear may further include an actuator configured to be actuated to facilitate rotation of the first shield relative to the outer shell.

In one aspect, the protective headwear may further include an actuator configured to be actuated to facilitate removal of the first shield from the outer shell.

In one aspect, the actuator may be configured to be actuated to facilitate rotation of the first shield relative to the outer shell.

In one aspect, the protective headwear may further include a first actuator configured to be actuated to facilitate rotation of the first shield relative to the outer shell and a second actuator configured to be actuated to facilitate removal of the first shield from the outer shell.

In one aspect, the protective headwear may further include an intermediate member coupled between the first shield and the outer shell. The intermediate member and the first shield may be rotatable together relative to the outer shell, and the intermediate member may remain coupled to the outer shell with the first shield removed.

In one aspect, the first shield may completely cover the second shield in the first position and the first shield may expose at least a portion of the second shield in the second position.

In one aspect, the first shield may have a first viewing capacity and the second shield may have a second viewing capacity greater than the first viewing capacity.

In one aspect, the outer shell may include a front, a rear opposite the front, a right side and a left side opposite the right side. The first shield may be coupled to the front of the outer shell and may be removed from the outer shell by moving the first shield in a direction out from the front of the outer shell along an axis extending from the rear toward the front of the outer shell.

In one aspect, the first shield may rotate relative to the outer shell about a first axis, and the first shield may be removed from the outer shell along a second axis transverse to the first axis.

In one aspect, the first shield may rotate relative to the outer shell about a first axis, and the first shield may be removed from the outer shell along a second axis perpendicular to the first axis.

In one aspect, the protective headwear may be a welding helmet.

In one aspect, a protective headwear is provided and includes a shell defining an opening in a front thereof, a first shield coupled to the outer shell and moveable between a first position and a second position, and a second shield. The first shield has a first viewing capacity. The second shield is coupled to the outer shell over the opening. The first shield covers the second shield to a greater extent in the first position than in the second position, and the second shield has a second viewing capacity greater than the first viewing capacity.

In one aspect, the first shield may be a welding shield at least partially limiting transparency there through and the second shield may be more transparent than the first shield.

In one aspect, the second shield may be continuous across the opening in the shell.

In one aspect, the second shield may be unitarily formed as one-piece.

In one aspect, the second shield may comprise at least thirty percent of a front surface area of the shell.

In one aspect, the second shield may be unitarily formed as one-piece.

In one aspect, the second shield may comprise between about thirty percent and about fifty percent of a front surface area of the shell.

In one aspect, the second shield may comprise between about thirty percent and about seventy-five percent of a front surface of the shell.

In one aspect, the second shield may be unitarily formed as one-piece.

In one aspect, the protective headwear may be a welding helmet.

In one aspect, a method of manufacturing a protective headwear is provided. The method includes forming a resilient, arcuate and at least partially transparent shield as a unitary single-piece having a front surface, a rear surface opposite the front surface, a right end and a left end opposite the right end. The rear surface is concave and a distance is defined between the right and left ends with the shield in an at rest position. The method also includes forming a shell defining an opening through the shell and coupling the resilient, arcuate and at least partially transparent shield to the shell.

In one aspect, the distance is a first distance, and coupling may further include moving the right and left ends of the shield away from each other to provide a second distance between the right and left ends greater than the first distance. Coupling may further include positioning the shield over the opening in the shell with the shield providing the second distance between the right and left ends, releasing the right and left ends of the shield to allow the right and left ends to move toward the at rest position, and engaging an exterior surface of the shell with the shield after releasing the right and left ends of the shield. A width of the shell defined by locations where the right and left ends of the shield engage the shell may be greater than the first distance and less than the second distance.

In one aspect, coupling may further include applying a compressive force to the exterior of the shell with the shield.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
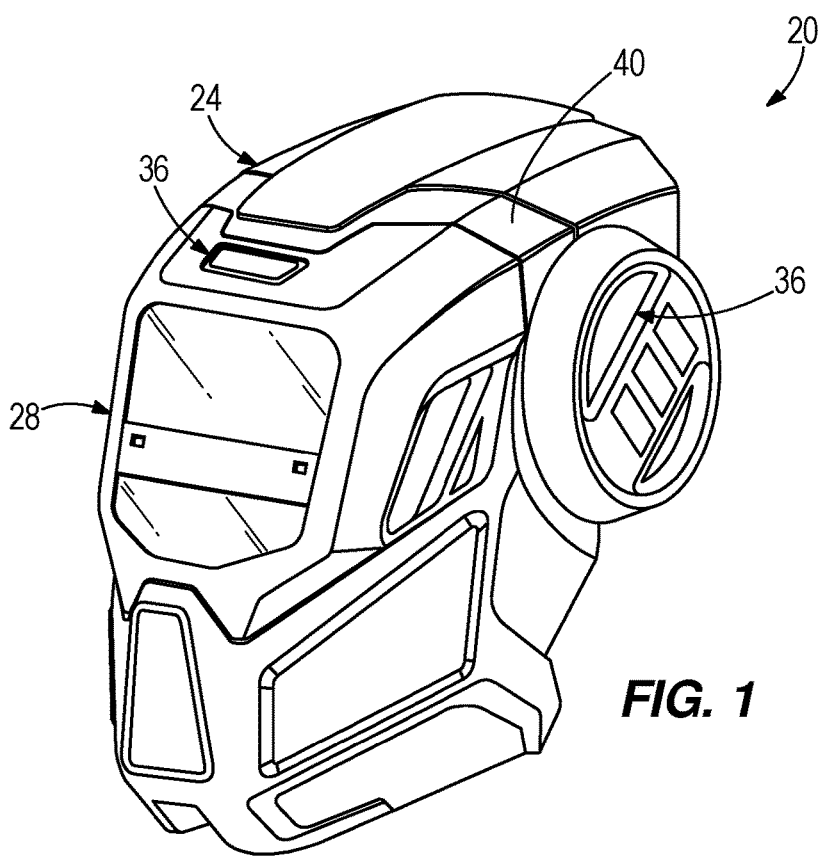
FIG. 1 is a top, front perspective view of one example of a protective headwear including one example of a first shield and one example of an actuator for allowing movement of the first shield between multiple positions, according to one aspect of the present disclosure.

Referring to FIGS. 1-4, one example of a protective headwear 20 is illustrated. In this illustrated example, the protective headwear 20 is a welding helmet. In other examples, the protective headwear may be other types of protective headwear including, but not limited to, hard hats, bicycle helmets, military helmets, grinding shields, or any other type of headwear capable of providing protection to a wearer's head.

In the illustrated example, the protective headwear 20 includes an outer shell 24, a first shield 28, a second shield 32 (beneath the first shield 28) (see FIG. 2), an actuator 36, and headgear within the outer shell 24 to support the protective headwear 20 on a wearer's head. The first shield 28 may be a welding shield and is coupled to the outer shell 24 over the second shield 32. The first shield 28 is darkened or capable of darkening in order to inhibit damage to a wearer's eyes while performing a welding process. In one example, the first shield 28 is an auto-darkening welding shield.

The second shield 32 is coupled to the outer shell 24 beneath the first shield 28 and is darkened less than the first shield 28. In one example, the second shield 32 has no tinting or darkening and is completely transparent. In one example, the second shield 32 is a clear polycarbonate lens or shield. The second shield 32 may be referred to as a grinding shield. In one example, the second shield 32 is manufactured or formed to have an arcuate shape when at rest. In one example, the second shield is arcuately formed to have a narrower curvature or smaller curve radius than a curvature or curve radius of a front of the outer shell 24. In this example, the second shield 32 is coupled to the outer shell 24 by deflecting the second shield 32 outward at its ends to a larger curvature or curve radius than the front of the outer shell 24, properly positioning the second shield 32 on the outer shell 24 over opening 38 defined in the front of the outer shell 24, and releasing the ends of the second shield 32 to allow the resiliency of the second shield to move the second shield 32 towards its at rest curvature or curve radius. Since the curvature or curve radius of the front of the outer shell 24 is greater than the curvature or curve radius of the second shield 32 in the at rest position, the second shield 32 is not allowed to return to its at rest position. Thus, the second shield 32 applies a compression force to the outer shell 24 to assist with coupling the second shield 32 to the outer shell 24 and maintaining the second shield 32 on the outer shell 24. The second shield 32 may have any curvature or curve radius and all of such possibilities are intended to be within the spirit and scope of the present disclosure. In some examples, the curvature or curve radius of the second shield 32 may be selected based on an amount of compression force desired for the second shield 32 to apply to the outer shell 24. The protective headwear 20 includes a plurality of retaining or coupling members 39 to assist with coupling the second shield to the outer shell 24. The second shield also provides a wide viewing angle for wearers of the protective headwear.

Figure 2:
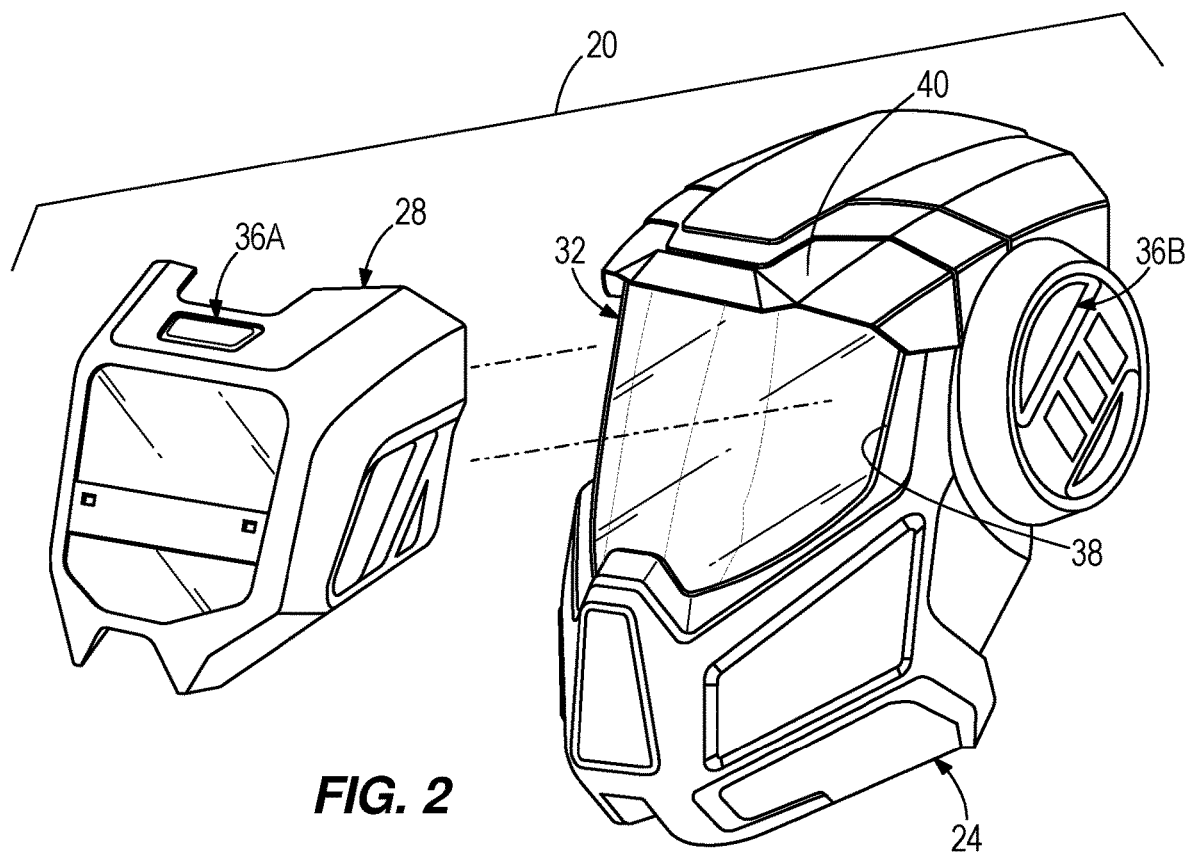
FIG. 2 is a top, front perspective view of the protective headwear shown in FIG. 1 with the first shield shown in a removed position from an outer shell of the protective headwear, according to one aspect of the present disclosure.

With continued reference to FIGS. 1-4, the first shield 28 is moveable between a plurality of positions. In FIG. 1, the first shield 28 is shown in a first, a downward or an operative position, in which the first shield 28 covers the second shield 32 and a wearer must view through both the first shield 28 and the second shield 32. The first shield 28 is commonly in the first position when the protective headwear 20 is used for a welding process and it is desirable to protect a wearer's eyes from damage by viewing a welding arc. In FIG. 2, the first shield 28 is shown in a second or removed position, in which the first shield 28 is completely removed from the outer shell 24 to expose the second shield 32. The first shield 28 may be removed from the outer shell 24 when a wearer is not performing a welding process and wishes to have an unimpeded view through the protective headwear 20. Wearer's may perform other functions or processes with the first shield 28 removed such as, for example, grinding, cutting, working with tools, manipulating objects, or any other non-welding process. By removing the first shield 28 from the outer shell 24, the overall weight of the protective headwear 20 is significantly decreased, thereby making the protective headwear 20 more comfortable to wear and decreasing the stress or pressure applied to the wearer's head, neck and body. Technology included in the first shield 28 or welding shield to provide the necessary tinting or darkening may add significant weight to the first shield 28. For example, auto-darkening welding shields are often heavy and represent a considerable portion of the overall weight of the protective headwear 20. Thus, by removing the first shield 28, the overall weight of the protective headwear 20 is significantly reduced.

Figure 3:
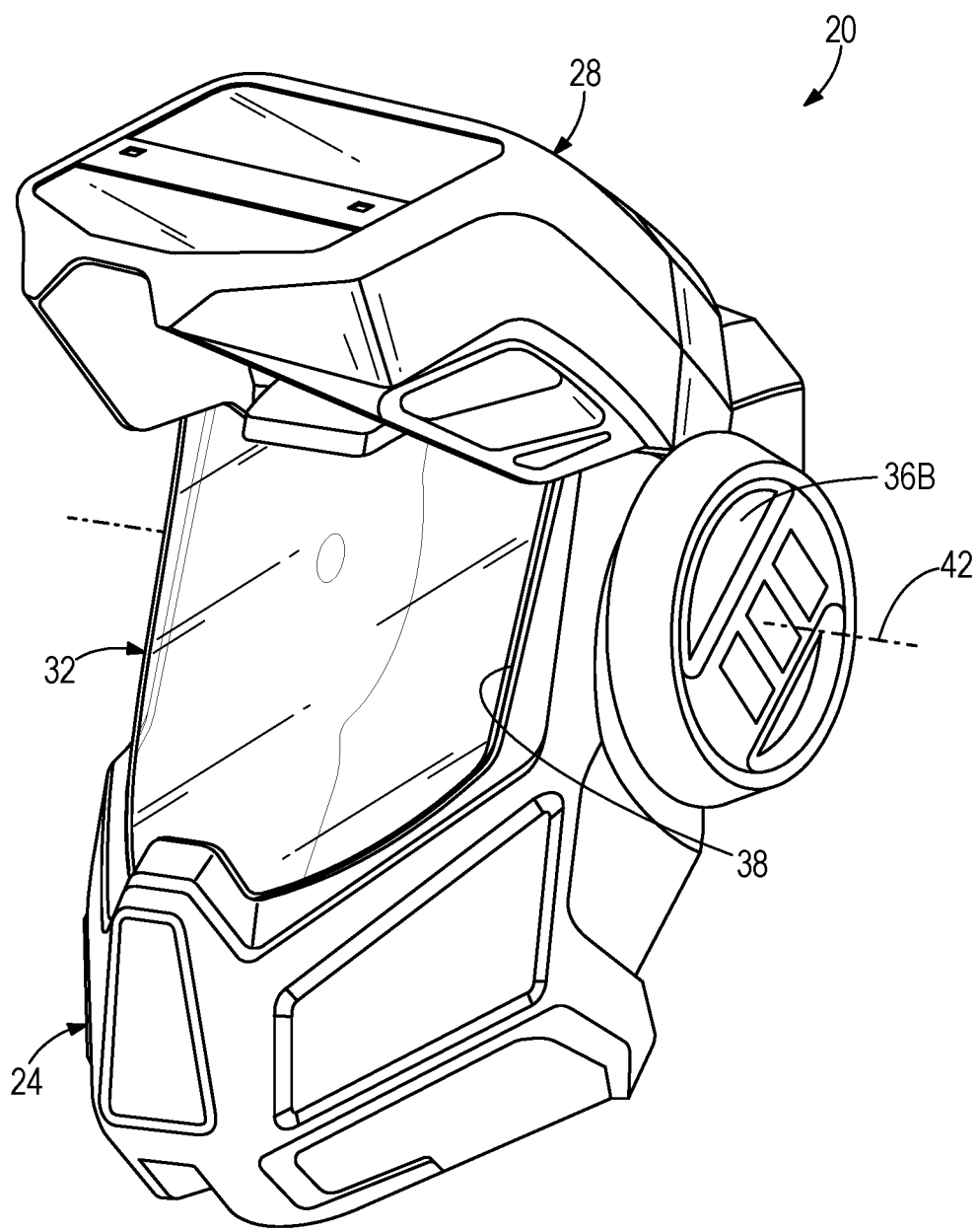
FIG. 3 is a top, front perspective view of the protective headwear shown in FIG. 1 with the first shield shown in an upwardly rotated or inoperative position relative to the outer shell of the protective headwear, according to one aspect of the present disclosure.

With particular reference to FIG. 3, the first shield 28 is shown in a third, a rotated or an inoperative position, in which the first shield 28 is rotated upward relative to the outer shell 24, no longer covers the second shield 32, and remains coupled to the outer shell 24. The first shield 28 rotates about an axis 42. In one example, pivots may be located at locations where the axis 42 intersects the first shield 28. In one example, the axis 42 may be co-linear or a same axis about which the outer shell 24 rotates relative to headgear supported on a wearer's head. In one example, the axis 42 may be offset from and parallel to an axis about which the outer shell 24 rotates relative to headgear. In one example, the axis 42 may be transverse to an axis about which the outer shell 24 rotates relative to headgear.

The first shield 28 may be rotated to the third position when a wearer is not performing a welding process and wishes to have an unimpeded view through the protective headwear 20. Wearer's may perform similar functions to those described above in connection with the second position of the first shield 28 with the first shield 28 in the third or rotated position. Rotating the first shield 28 to the third or rotated position allows a wearer to maintain the first shield 28 coupled to the outer shell 24, but still have an unimpeded view through the second shield 32. In one example, a wearer may desire to move the first shield 28 to the rotated position rather than the removed position if the wearer is only taking quick breaks between welding processes. A wearer may not desire to completely remove the first shield 28 if the wearer will be requiring the first shield 28 often. Thus, the protective headwear 20 illustrated in FIGS. 1-4 provides multiple functionalities, thereby improving a wearer's experience and capabilities to easily perform multiple functions.

The protective headwear 20 is capable of including more than three positions for the first shield 28 and all of such possibilities are intended to be within the spirit and scope of the present disclosure. For example, the first shield 28 may be selectively secured at numerous locations between the first or operative position shown in FIG. 1 and the third or rotated position shown in FIG. 3. This provides a wearer with increased selectability of how and where the first shield 28 is located relative to the outer shell 24.

The first shield 28 may be moved between and secured in the plurality of positions relative to the outer shell 24 in a variety of manners and any and all of such possibilities are intended to be within the spirit and scope of the present disclosure. The following examples of components and manners used to move and secure the first shield 28 in the plurality of positions are only examples of the many possibilities and are not intended to be limiting upon the present disclosure. These examples are provided to demonstrate at least some of the principles of the present disclosure.

With reference to FIGS. 1-4, the actuator 36 may be comprised of a first actuator 36A and a second actuator 36B. The first actuator 36A is positioned on the first shield 28 and engages a visor or intermediate member 40 coupled to the outer shell 24. The first actuator 36A may be actuated to remove the first shield 28 from the visor 40 and the outer shell 24 of the protective headwear 20. To couple the first shield 28 to the visor 40 and outer shell 24, the first shield 28 is aligned with the visor 40 and slid onto the visor 40 until the first actuator 36A recouples to the visor 40. In one example, the first actuator 36A may comprise a latch buckle. In another example, the first actuator 36A may comprise a lever. In this example, the first actuator 36A may include a spring loaded button that is depressible to engage one end of the lever, thereby raising the other end of the lever to release or disengage a latch, projection or recess to ultimately allow removal of the first shield 28 from the visor 40 and the outer shell 24. In another example, the protective headwear 20 may not include a visor and the first shield 28 may be coupled directly to the outer shell 24. Any of the above-described and other possible types of actuators and manners of removing and coupling the first shield 28 to the visor 40 also apply to removing and coupling the first shield 28 to the outer shell 24. In such an example, the first actuator 36A may engage the outer shell 24.

The second actuator 36B is coupled to a side of the outer shell 24 and may be actuated to rotate the first shield 28 relative to the outer shell 24. In one example, the first shield 28 may rotate with the visor 40 relative to the outer shell 24. In another example, the first shield 28 may rotate relative to the visor 40 and the outer shell 24. The first shield 28 may be rotated to a completely upwardly rotated position shown in FIG. 3 or the first shield 28 may be rotated to any number of intermediate positions between the fully downward position shown in FIG. 1 and the fully upward position shown in FIG. 3. In the illustrated example, in FIG. 3, the second actuator 36B may be actuated and the wearer may rotate the first shield 28 and the visor 40 upward to the rotated position. The first shield 28 and the visor 40 may be positively secured when in the third or rotated position. Additionally, in other examples, the first shield 28 and the visor 40 may be positively secured when in any of the intermediate positions between the fully downward position and the fully upward position. The second actuator 36B may be actuated again to rotate the first shield 28 and the visor 40 back toward the first or fully downward position. In one example, the protective headwear 20 may include a second actuator 36B on each side of the outer shell 24 to secure and release both sides of the visor 40. In one example, both second actuators 36B would be actuated to rotate the first shield 28 and the visor 40 to the third position. Likewise, both second actuators 36B would be actuated to rotate the first shield 28 and the visor 40 from the third position to the first position. In another example, the protective headwear 20 includes one second actuator 36B and only the single second actuator 36B is actuated to facilitate rotation of the first shield 28 relative to the outer shell 24.

It should be understood that the actuators described and illustrated herein are only exemplary actuators. The protective headwear 20 is capable of including any type of actuator and all of such actuator possibilities are intended to be within the spirit and scope of the present disclosure. For example, the actuators may be detent type actuators, spring biased actuators, projection and recess actuators, ratchet type actuators, latch actuators, latch buckle actuators, friction-based actuators, or any other type of actuator. Furthermore, the actuators may be actuated in any manner and all of such actuation possibilities are intended to be within the spirit and scope of the present disclosure. For example, the actuators may be pressed or depressed, slid, rotated, touch screen, conductive, or any other type of actuation.

In another example, the protective headwear 20 may include a single actuator for both removing and rotating the first shied 28 relative to the outer shell 24. In such an example, the actuator may include multiple positions, at least one position for removing the first shield 28 from the outer shell 24 and at least one position for rotating the first shield 28 relative to the outer shell 24. In other words, the single actuator may be configured to be actuated to a first position to allow removal of the first shield 28 from the outer shell 24, and to be actuated a second position to allow rotation of the first shield 28 relative to the outer shell 24.

The protective headwear 20 provides the capability of moving, rotating and removing the first shield 28 without the use of tools. This allows a wearer to quickly remove and reattach the first shield 28 as desired, thereby saving time and increasing the chance that the wearer actually removes the first shield 28, which ultimately improves the wearer's work experience and posture (e.g., due to carrying around less weight on their head).

Figure 4:
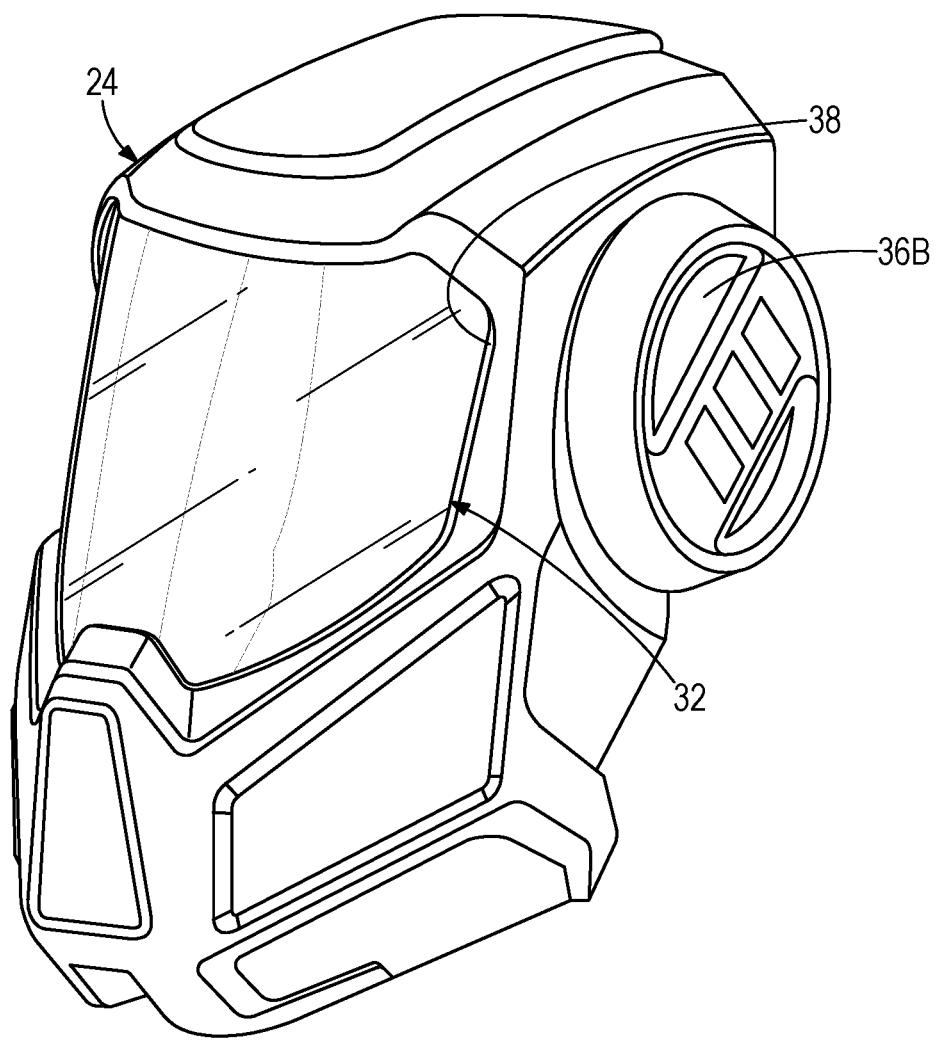
FIG. 4 is a top, front perspective view of the protective headwear shown in FIG. 1 with the first shield and a visor removed from the outer shell to expose a second shield coupled to the outer shell, according to one aspect of the present disclosure.

With particular reference to FIG. 4, the visor 40 may be removed from the outer shell 24 along with the first shield 28. In one example, the visor 40 may be removed by actuating the second actuator 36B in a manner different than it is actuated to allow rotation of the first shield 28 and the visor 40 to the third position. For example, the second actuator 36B may be depressed a different extent or amount than the second actuator 36B is depressed to rotate the first shield 28 relative to the outer shell 24. In another example, the protective headwear 20 may include two second actuators 36B, one on each side of the outer shell 24. In such an example, one of the second actuators 36B may be actuated to rotate the first shield 28 relative to the outer shell 24 and the other second actuator 36B may be actuated to remove the visor 40 from the outer shell 24. In other words, one of the actuators 36B may be configured to be actuated to a first position to allow removal of the first shield 28 from the outer shell 24, and another of the actuators 36B may be actuated to a second position to allow rotation of the first shield 28 relative to the outer shell 24.

Figure 6:
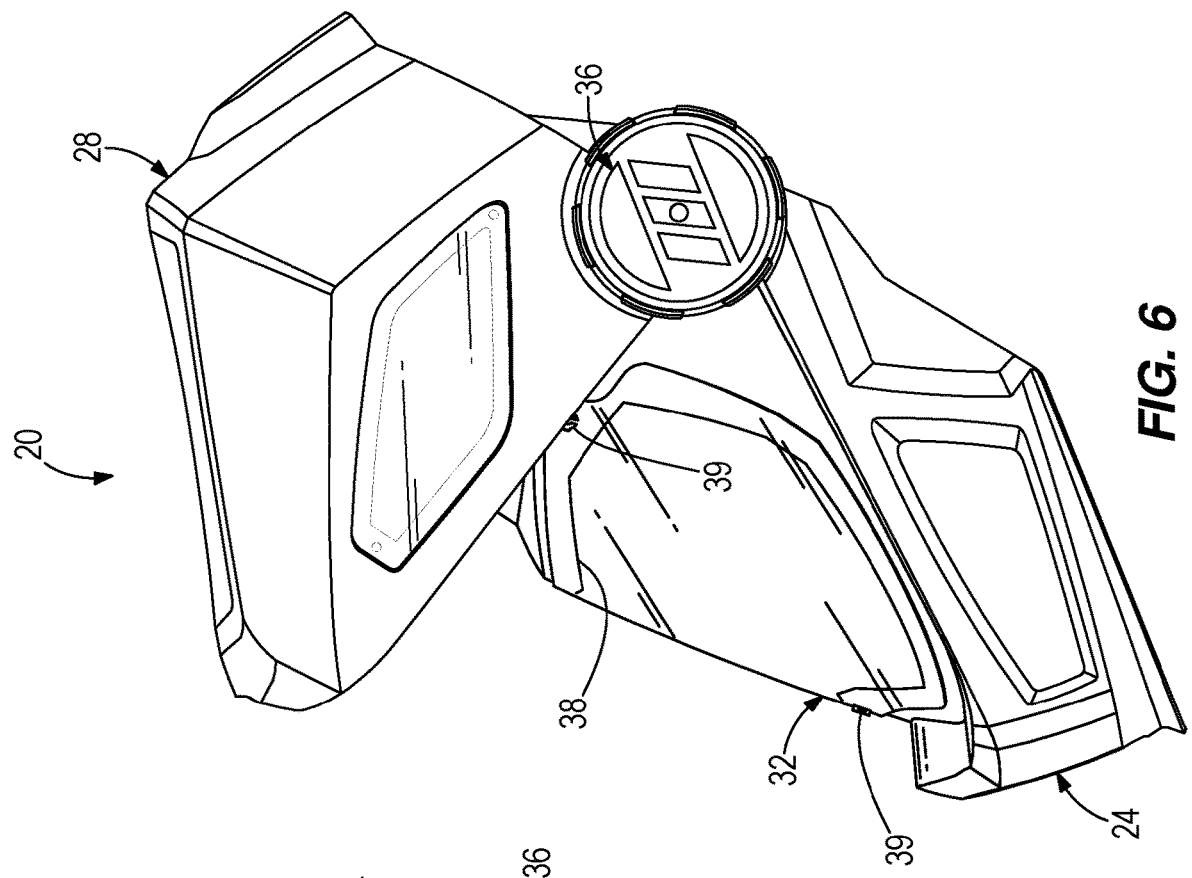
FIG. 6 is a side view of the protective headwear shown in FIG. 5 with the first shield shown in an upwardly rotated or inoperative position, according to one aspect of the present disclosure.
Figure 5:
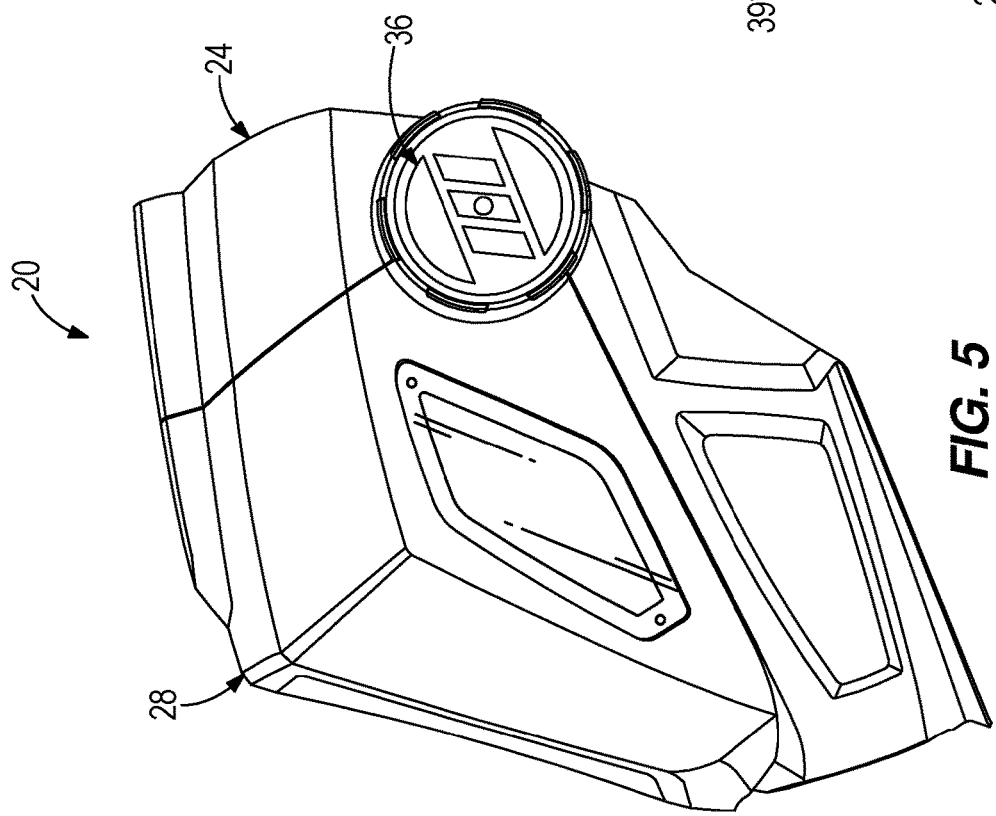
FIG. 5 is a side view of another example of a protective headwear with a first shield shown in a downward, operating position, according to one aspect of the present disclosure.
Figure 7:
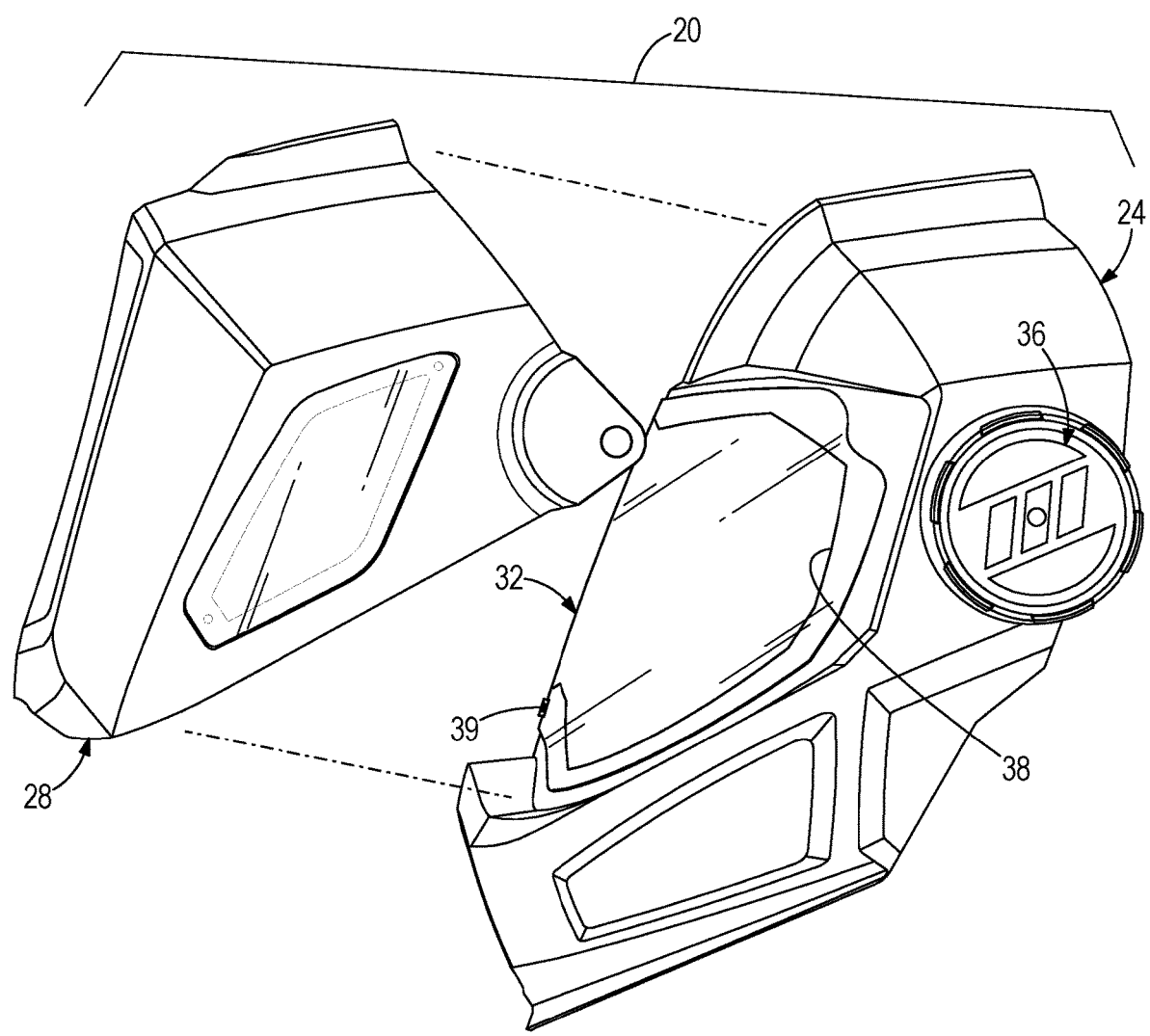
FIG. 7 is a side view of the protective headwear shown in FIG. 5 with the first shield shown in another inoperative or a removed position, according to one aspect of the present disclosure.

With reference to FIGS. 5-7, another example of a protective headwear 20 is shown and includes a first shield 28 that is rotatable relative to and selectively removable from an outer shell 24. In this example, the protective headwear 20 does not include a visor and the first shield 28 is connected directly to the outer shell 24. The first shield 28 is rotatable relative to the outer shell 24 (e.g., as shown in FIG. 6) and may be positioned at any number of positions between a fully downward position (see FIG. 5) and a fully upward position (see FIG. 6). The first shield 28 may also be removed from the outer shell 24 as shown, for example, in FIG. 7. The first shield 28 may be rotated relative to and removed from the outer shell 24 in any manner and all of such manners are intended to be within the spirit and scope of the present disclosure.

Figure 8:
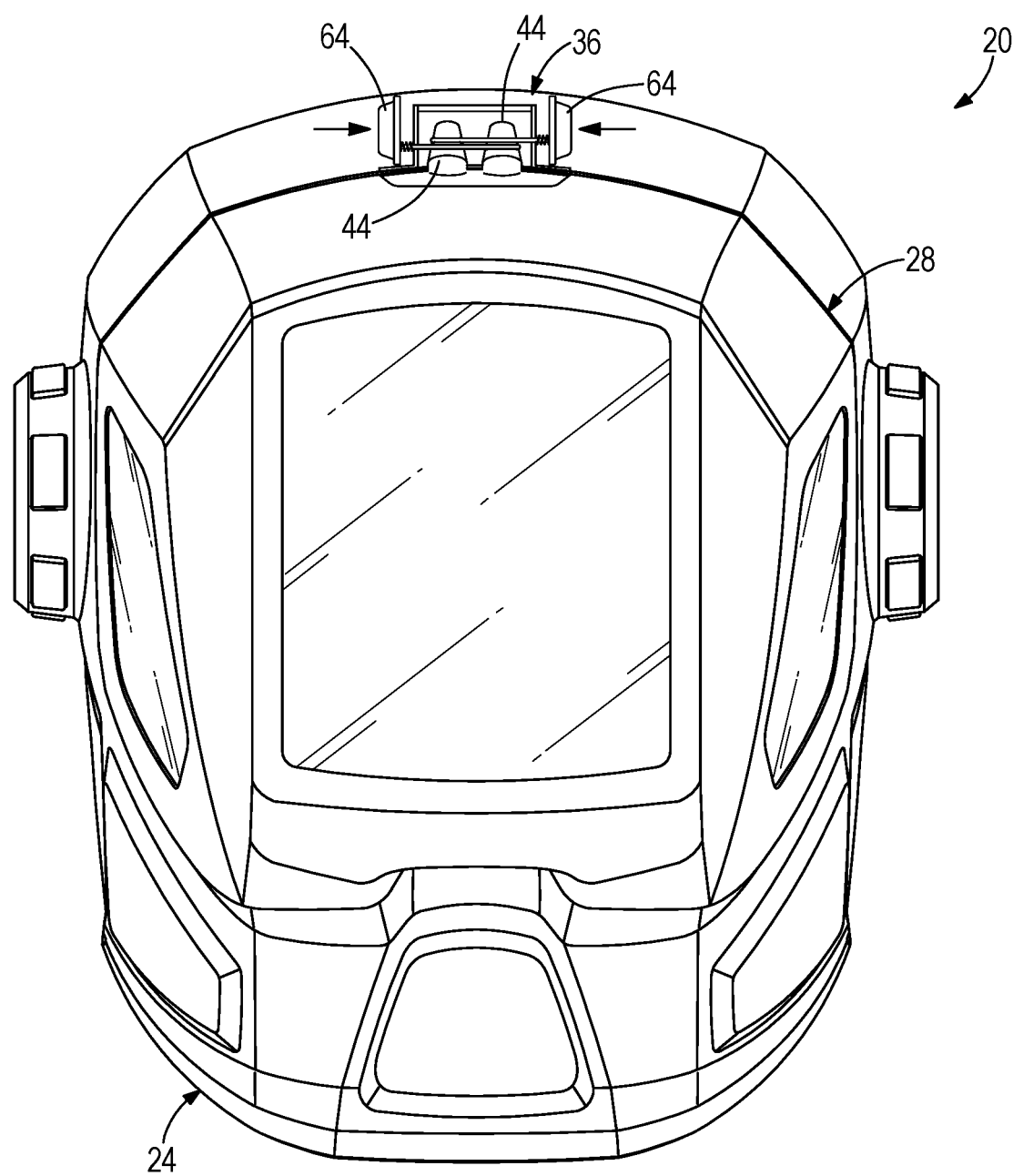
FIG. 8 is a front view of another example of a protective headwear including another example of an actuator for allowing movement of a first shield between multiple positions, according to one aspect of the present disclosure.
Figure 9:
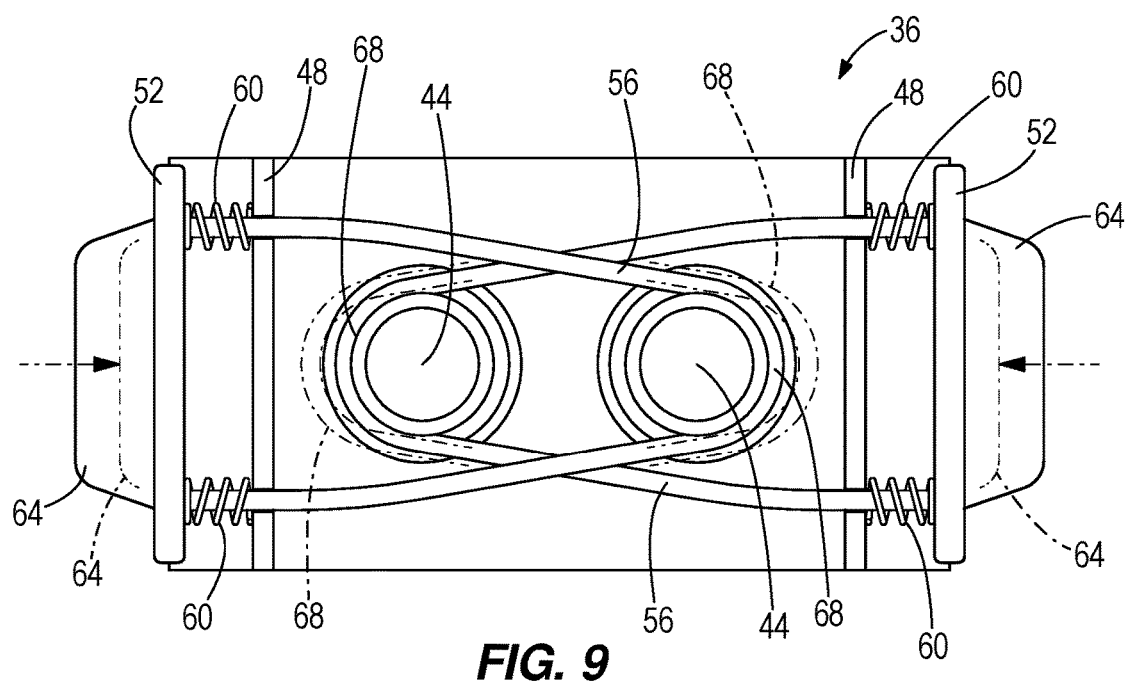
FIG. 9 is an enlarged front view of the actuator shown in FIG. 8, according to one aspect of the present disclosure.
Figure 10:
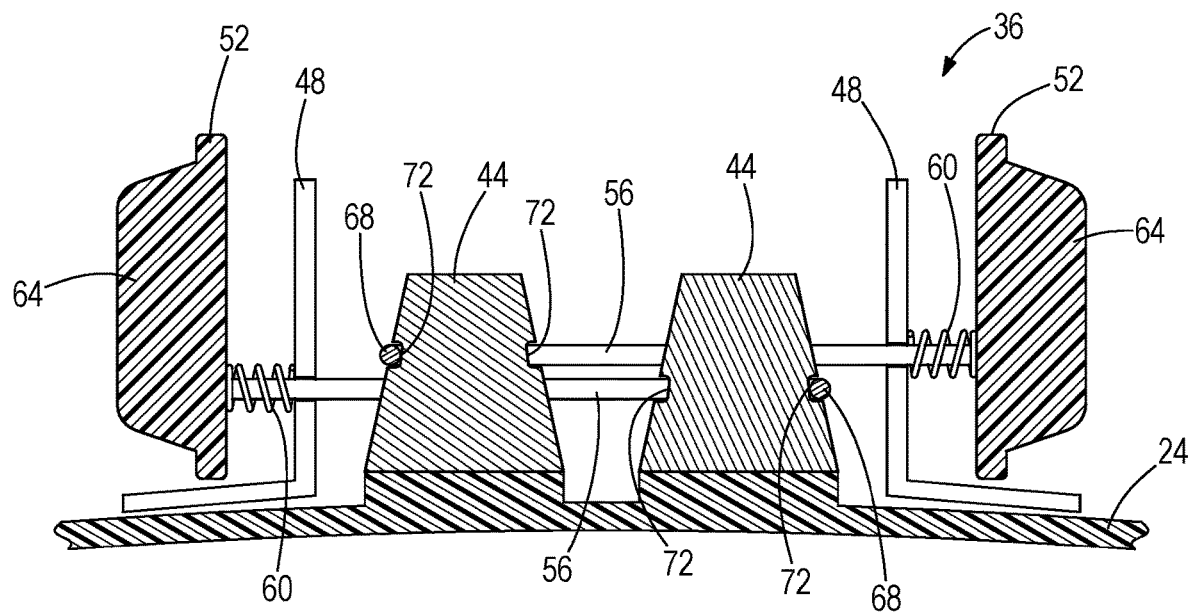
FIG. 10 is a partial cross-sectional view of the actuator and a portion of an outer shell of the protective headwear shown in FIG. 8, according to one aspect of the present disclosure.

Referring now to FIGS. 8-10, another example of an actuator 36 for allowing the first shield 28 to move relative to the outer shell 24 is illustrated. In this example, the actuator 36 includes a pair of projections or posts 44 fixed or coupled to the outer shell 24 of the protective headwear 20 and a variety of other components coupled to the first shield 28. These components include a pair of inner flanges 48 fixed to the first shield 28, a pair of outer flanges 52 moveable relative to the inner flanges 48, a coupling member or ring 56 coupled to each of the outer flanges 52 and moveable with the respective outer flange 52, at least one biasing member 60 coupled to each ring 56 and positioned between the inner and outer flanges 48, 52, and a push button 64 coupled to an outer surface of each of the outer flanges 52. When the first shield 28 is secured to the outer shell 24, the rings 56 wrap around the projections 44 and an end 68 of each of the rings 56 is positioned in a recess 72 defined in the projection 44 furthest from the push button 64 associated with the ring 56. In the illustrated example, the projections 44 are frusto-conical or tapered in shape. To move the first shield 28 relative to the outer shell 24, a wearer pinches or presses the push buttons 64 toward each other, which causes the rings 56 to move laterally in opposite directions and remove from the respective recesses 72 defined in the projections 44. When the rings 56 are clear of the recesses 72, the first shield 28 may be moved relative to the outer shell 24. In one example, actuating the actuator 36 in this manner allows a wearer to remove the first shield 28 from the outer shell 24. In another example, actuating the actuator 36 in this manner allows a wearer to rotate the first shield 28 relative to the outer shell 24. In a further example, actuating the actuator 36 in this manner allows a wearer to both remove the first shield 28 from the outer shell 24 and rotate the first shield 28 relative to the outer shell 24.

Figure 11:
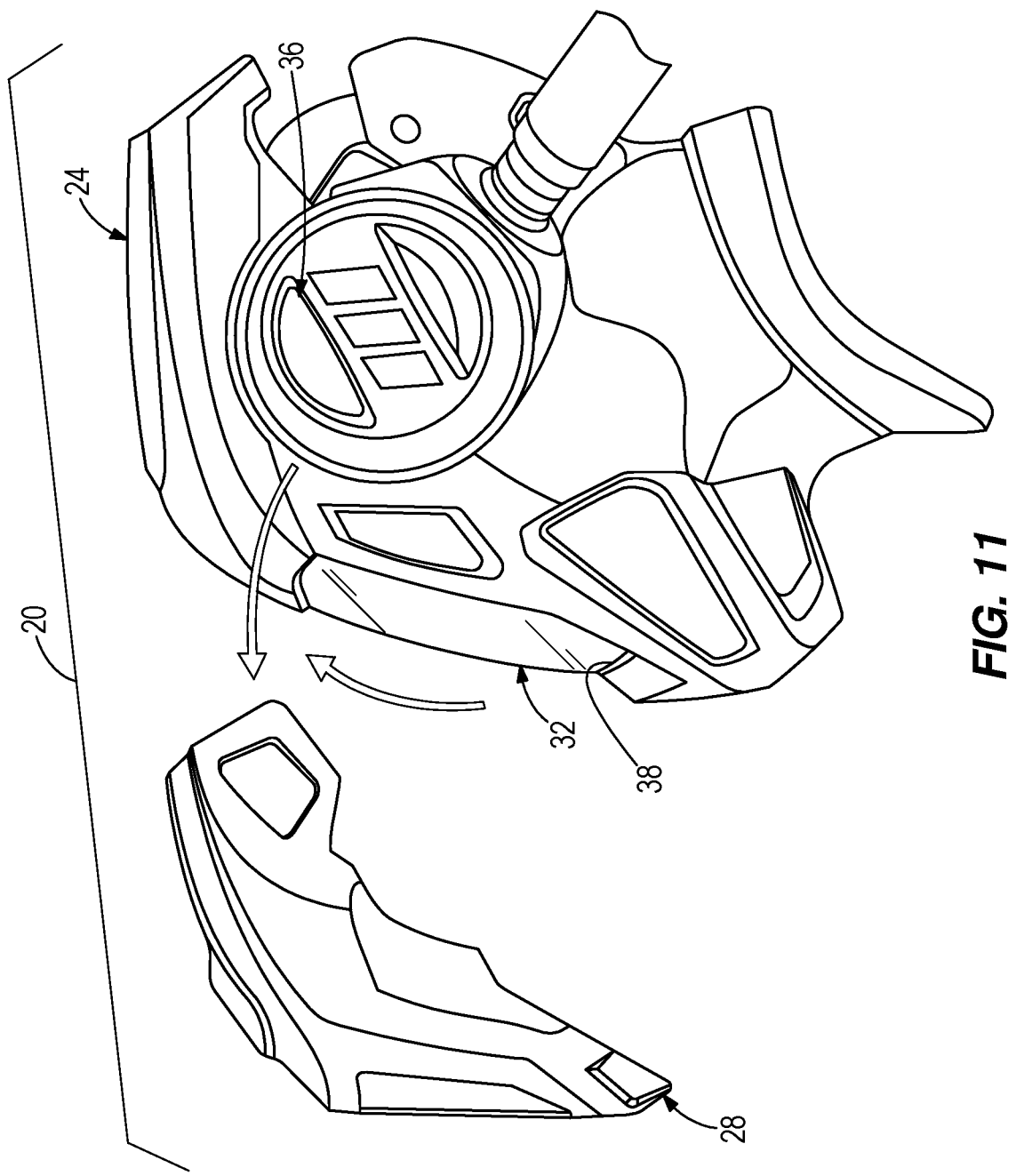
FIG. 11 is a side view of another example of a protective headwear with a first shield that is both rotatable relative to and removable from an outer shell of the protective headwear, according to one aspect of the present disclosure.

Referring now to FIG. 11, another example of an actuator 36 for allowing the first shield 28 to move relative to the outer shell 24 is illustrated. The actuator 36 illustrated in FIG. 11 is located in a similar position to the second actuator 36B illustrated in FIGS. 1-4. In one example, actuating the actuator 36 allows a wearer to remove the first shield 28 from the outer shell 24. In another example, actuating the actuator 36 allows a wearer to rotate the first shield 28 relative to the outer shell 24. In a further example, actuating the actuator 36 in this manner allows a wearer to both remove the first shield 28 from the outer shell 24 and rotate the first shield 28 relative to the outer shell 24.

Figure 12:
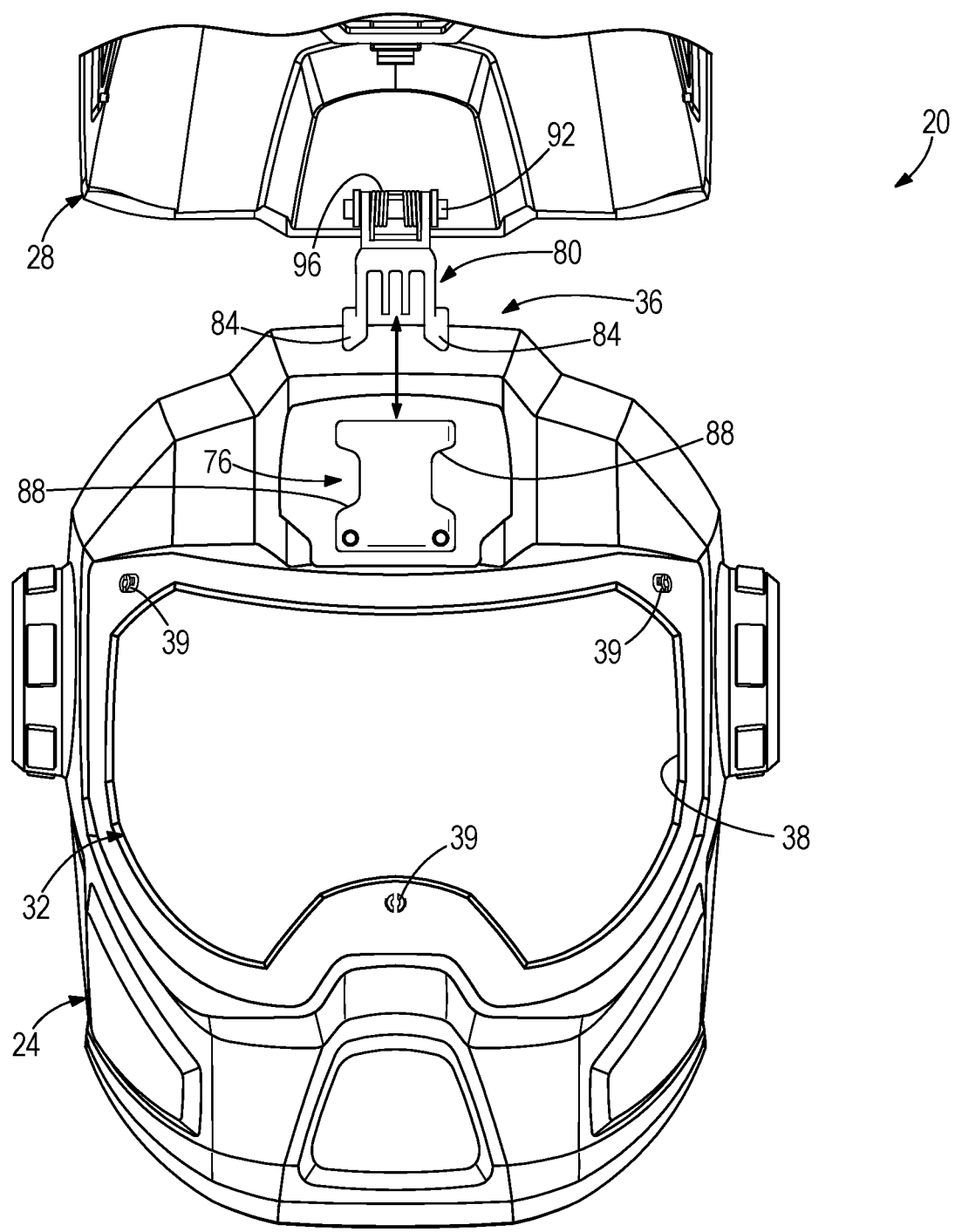
FIG. 12 is a front view of another example of a protective headwear including another example of an actuator for allowing movement of a first shield between multiple positions, according to one aspect of the present disclosure.

Referring now to FIG. 12, another example of an actuator 36 for allowing the first shield 28 to move relative to the outer shell 24 is illustrated. In this example, the actuator 36 has a buckle-type configuration including a receiving member 76 secured to the outer shell 24 and an insertion member 80 secured to the first shield 28. In another example, the receiving member 76 may be secured to the first shield 28 and the insertion member 80 may be secure to the outer shell 24. The insertion member 80 is positively secured within the receiving member 76 when projections 84 on the insertion member 80 are positioned in receptacles 88 defined in the receiving member 76. A hinge or pivoting member 92 is coupled between the actuator 36 and the first shield 28. The hinge 92 allows the first shield 28 to rotate relative to the outer shell 24 between the first, operating position and the third, rotated position. To remove the first shield 28, a wearer depresses the projections 84 on the insertion member 80 to remove the projections 84 from the corresponding receptacles 88 in the receiving member 76 and then pulls the insertion member 80 out from the receiving member 76. With the insertion member 80 and the receiving member 76 uncoupled, the first shield 28 is removed from the outer shell 24. In one example, the actuator 36 and/or the hinge 92 may need to be actuated or otherwise manipulated to allow the first shield 28 to rotate about the hinge 92 between the first position and the third position. In one example, an over-center biasing member 96 may be utilized to assist with maintaining the first shield 28 in either the first position or the third position, depending on which side of center the first shield 28 is located.

Figure 13:
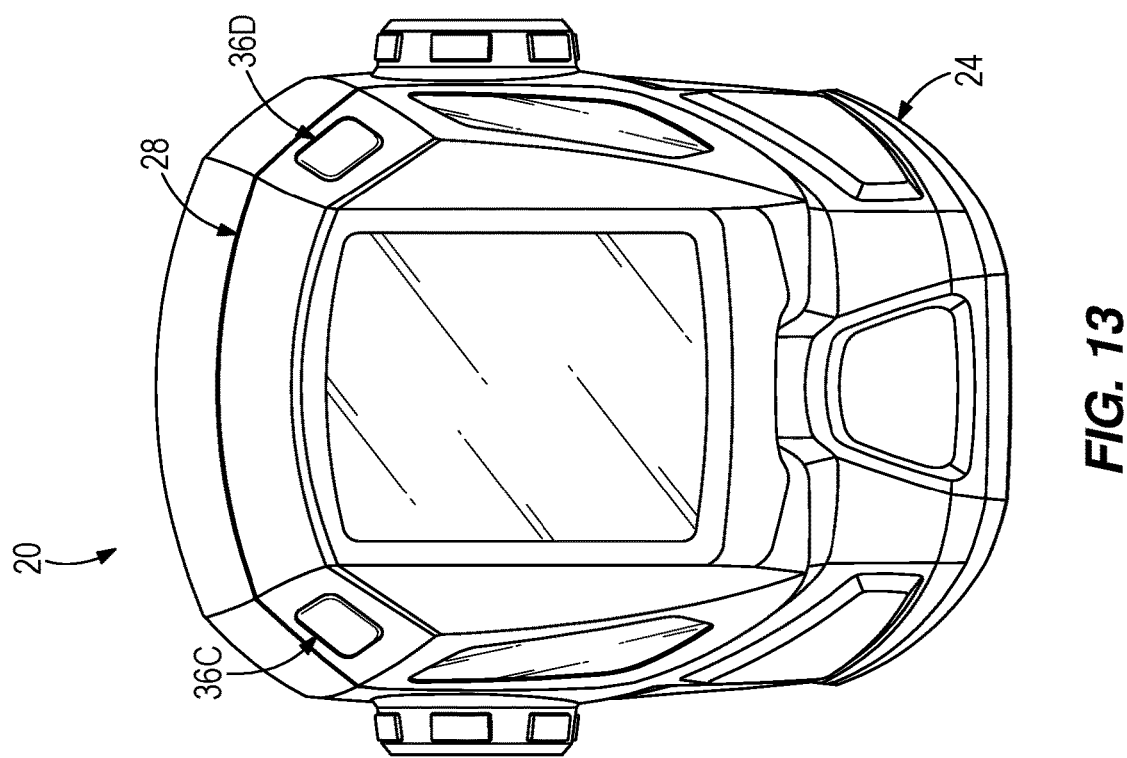
FIG. 13 is a front view of another example of a protective headwear including another example of an actuator for allowing movement of a first shield between multiple positions, according to one aspect of the present disclosure.

Referring now to FIG. 13, another example of an actuator 36 for allowing the first shield 28 to move relative to the outer shell 24 is illustrated. In this example, the actuator 36 includes a first actuator 36C on a first side of the protective headwear 20 and a second actuator 36D on a second side of the protective headwear 20. The first and second actuators 36C, 36D must both be actuated in order for the first shield 28 to move relative to the outer shell 24. In one example, actuating the first and second actuators 36C, 36D allows a wearer to remove the first shield 28 from the outer shell 24. In another example, actuating the first and second actuators 36C, 36D allows a wearer to rotate the first shield 28 relative to the outer shell 24. In a further example, actuating the first and second actuators 36C, 36D allows a wearer to both remove the first shield 28 from the outer shell 24 and rotate the first shield 28 relative to the outer shell 24.

Figure 14:
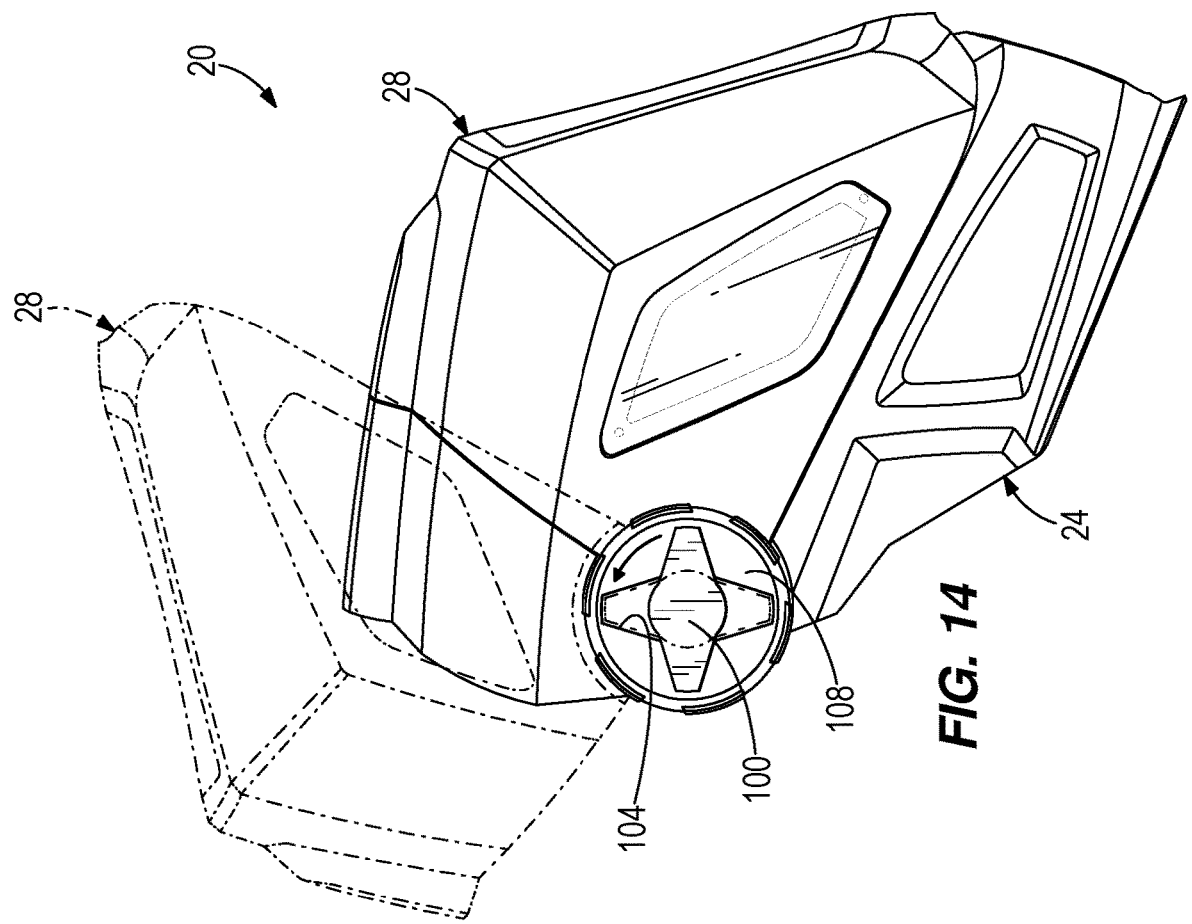
FIG. 14 is a side view of another example of a protective headwear including another example of an actuator for allowing movement of a first shield between multiple positions, according to one aspect of the present disclosure.
Figure 15:
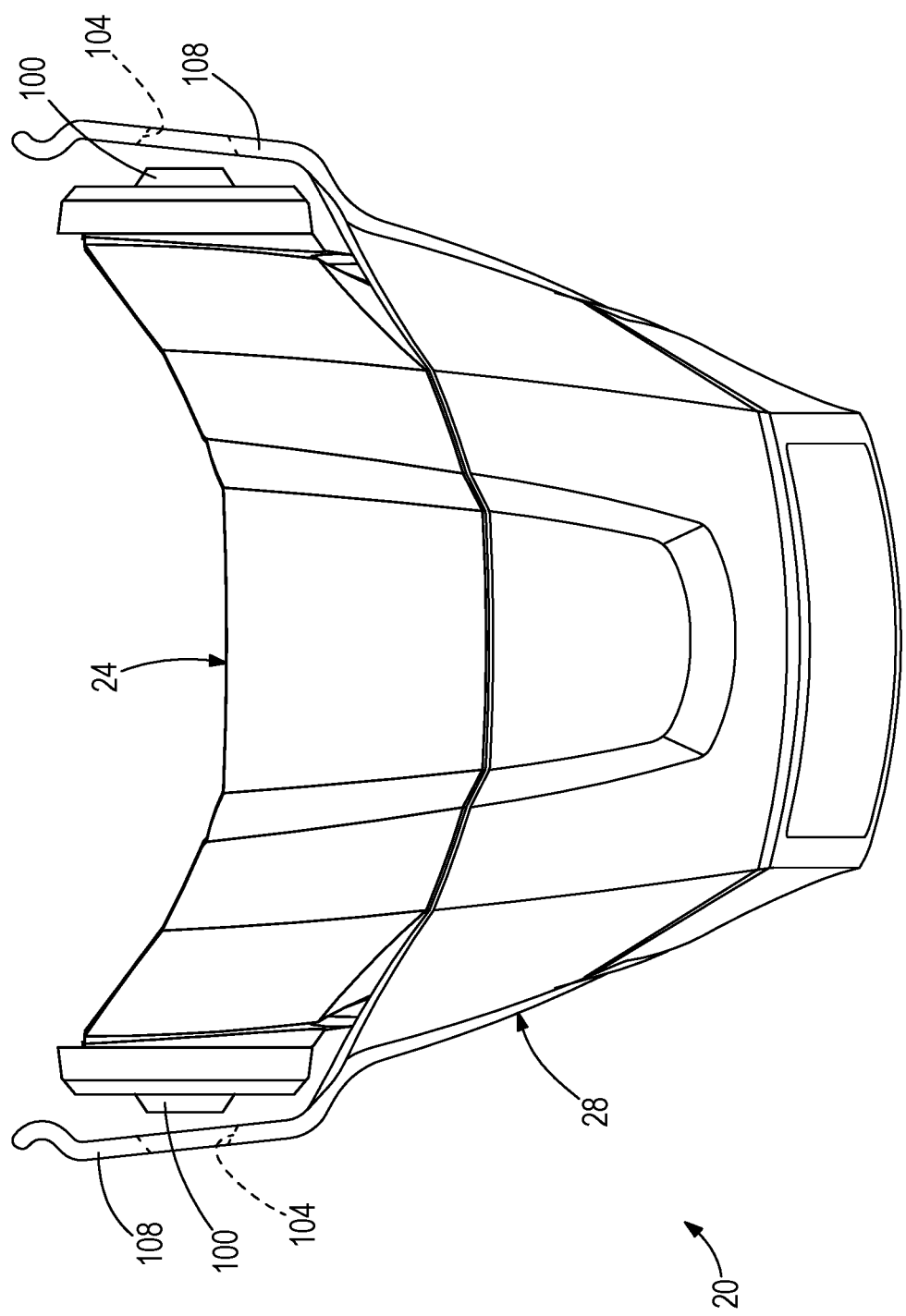
FIG. 15 is a top view of the protective headwear and actuator shown in FIG. 14 with the first shield removed from an outer shell of the protective headwear, according to one aspect of the present disclosure.
Figure 16:
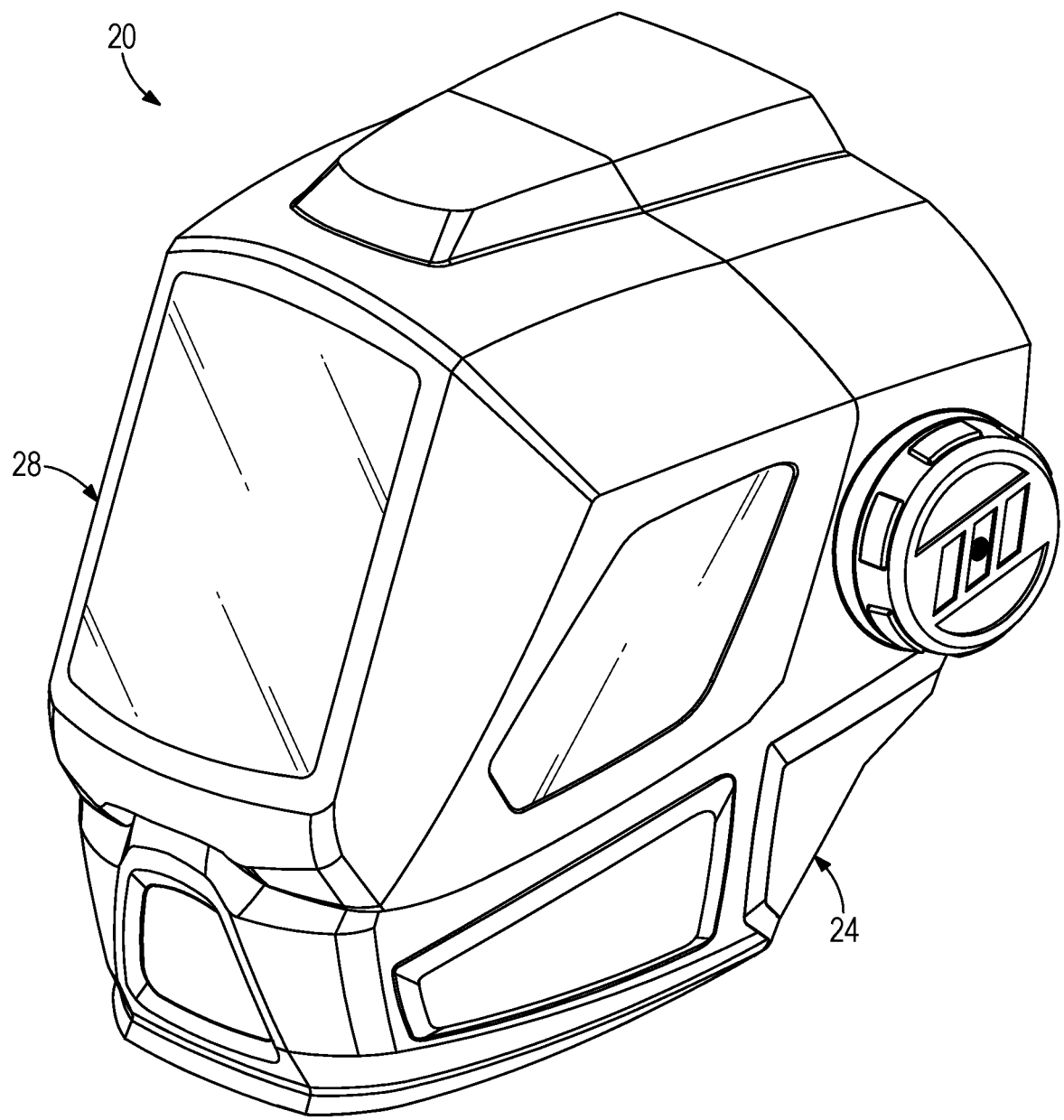
FIG. 16 is a top, front perspective view of another example of a protective headwear with a first shield of the protective headwear in a downward or operating position, according to one aspect of the present disclosure.

With reference to FIGS. 14 and 15, another example of a protective headwear 20 is illustrated. In this example, the outer shell 24 includes a pair of projections 100, one on each side of the outer shell 24, and the first shield 28 defines a pair of apertures 104, one on each side of the first shield 28. The projections 100 and the apertures 104 have complementary shapes that allow the projections 100 and the apertures 104 to act like keys or keyed elements.

With particular reference to FIG. 14, the first shield 28 is shown in the first or operative position, in which the projections 100 are positioned in the apertures 104 (only one side shown, but the other side is a mirror image) and the projections 100 and the apertures 104 are oriented in an offset manner to prevent side flanges 108 of the first shield 28 from being pulled outward and away from the outer shell 24, and past the projections 100. The first shield 28 may be rotated upward to the third position by a wearer grasping the first shield 28 and rotating it upward. The projections 100 act as a pivot or axle about which the first shield 28 rotates. To remove the first shield 28 from the outer shell 24, the first shield 28 must be rotated to the third position where the projections 100 and the apertures 104 are aligned in a complementary manner.

Referring now to FIG. 15, a wearer may then pull outward on the side flanges 108 and the aligned, complementary projections 100 and apertures 104 allow the side flanges 108 to pass by the projections 100. Once the side flanges 108 are beyond the projections 100, the first shield 28 may be removed from the outer shell 24. In this example, the material selected for the first shield 28 is sufficiently resilient to allow at least the side flanges 108 of the first shield 28 to deflect beyond the width of the projections 100 for removal and then return to its unbiased condition without permanently damaging the first shield 28. Additionally, the material and shape of the first shield 28 enable the first shield 28 to apply an appropriate amount of compression force to the outer shell 24 to couple the first shield 28 to the outer shell 24 and ensure sufficient friction to movement when the first shield 28 is in the first position, the third position or any position there between. Furthermore, the material of the first shield 28 is sufficient to meet protective headwear standards.

The projections 100 and the apertures 104 are complementarily shaped to achieve the above referenced function and are capable of having any complementary shapes to achieve the desired function. The illustrated and described shapes of the projections 100 and apertures 104 are provided to demonstrate principles of the present disclosure, but are not intended to be limiting upon the present disclosure. Rather, the projections 100 and apertures 104 are capable of have any complementary shapes that achieve the desired function and all of such possibilities are intended to be within the spirit and scope of the present disclosure.

In the example illustrated in FIGS. 14 and 15, the protective headwear 20 does not require an independent actuator to allow movement between a plurality of positions. Rather, the first shield 28 and the outer shell 24 include features that allow the first shield 28 to rotate relative to and remove from the outer shell 24.

Referring now to FIGS. 16-23, another example of a protective headwear 20 is illustrated. In the illustrated example, the protective headwear 20 includes an actuator 36 configured to allow the first shield 28 to move relative to an outer shell 24. Moreover, the actuator 36 is configured to allow the first shield 28 to rotate relative to the outer shell 24 and to be removed from the outer shell 24. The first shield 28 is moveable between a first, fully downward or operative position (see FIG. 16), a second, fully upward or first inoperative position (see FIGS. 17 and 18), and a third, removed or second inoperative position (see FIG. 19).

In the illustrated example, the actuator 36 includes a shell portion 120 and a shield portion 124. The shell portion 120 is coupled to the outer shell 24 and the shield portion 124 is coupled to the first shield 28. The shell portion 120 and the shield portion 124 are engageable to couple the first shield 28 to the outer shell 24. In the illustrated example, the shell portion 120 includes a channel 128 defining a pair of cavities 132, one cavity 132 on each side of the channel 128. A projection or catch 136 is defined in each cavity 132. The channel 128 includes an open top end 140 and an open bottom end 144. The open bottom end 144 allows debris positioned in the channel 128 to fall out from a bottom of the channel 128, thereby inhibiting collection or build-up of debris in the channel 128. The open top end 140 of the channel 128 is wider than the open bottom end 144 to provide a ramp to facilitate insertion of the shield portion 124 into the channel 128 and cavities 132 (described in more detail below).

The shield portion 124 includes a housing 148 defining a housing cavity 152 therein, a pair of aligned pin openings 156 defined in opposite sides of the housing 148, a pin 160 positioned in the pin openings 156 and extending through the housing 148, a biasing member 164 at least partially positioned in the housing cavity 152, a pair of support arms 168 extending from the housing 148, a coupling member 172 coupled to and supported by the support arms 168 and also coupled to the first shield 28, and an engagement member 176 coupled to the biasing member 164 and the coupling member 172.

Figure 20:
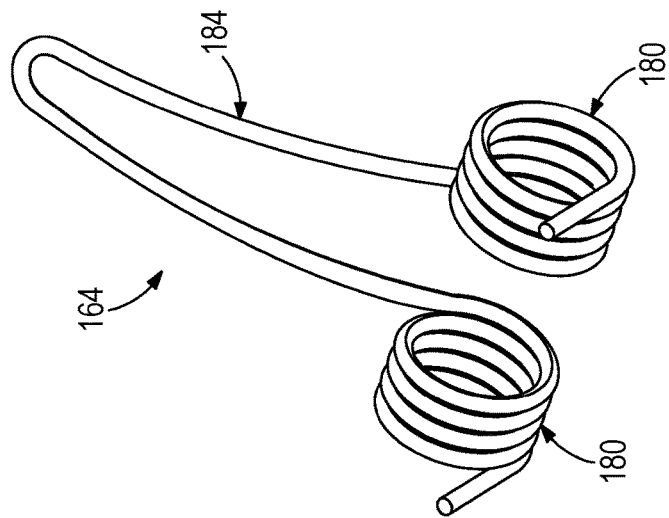
FIG. 20 is a perspective view of one example of a biasing member of one example of an actuator of the protective headwear, according to one aspect of the present disclosure.
Figure 21:
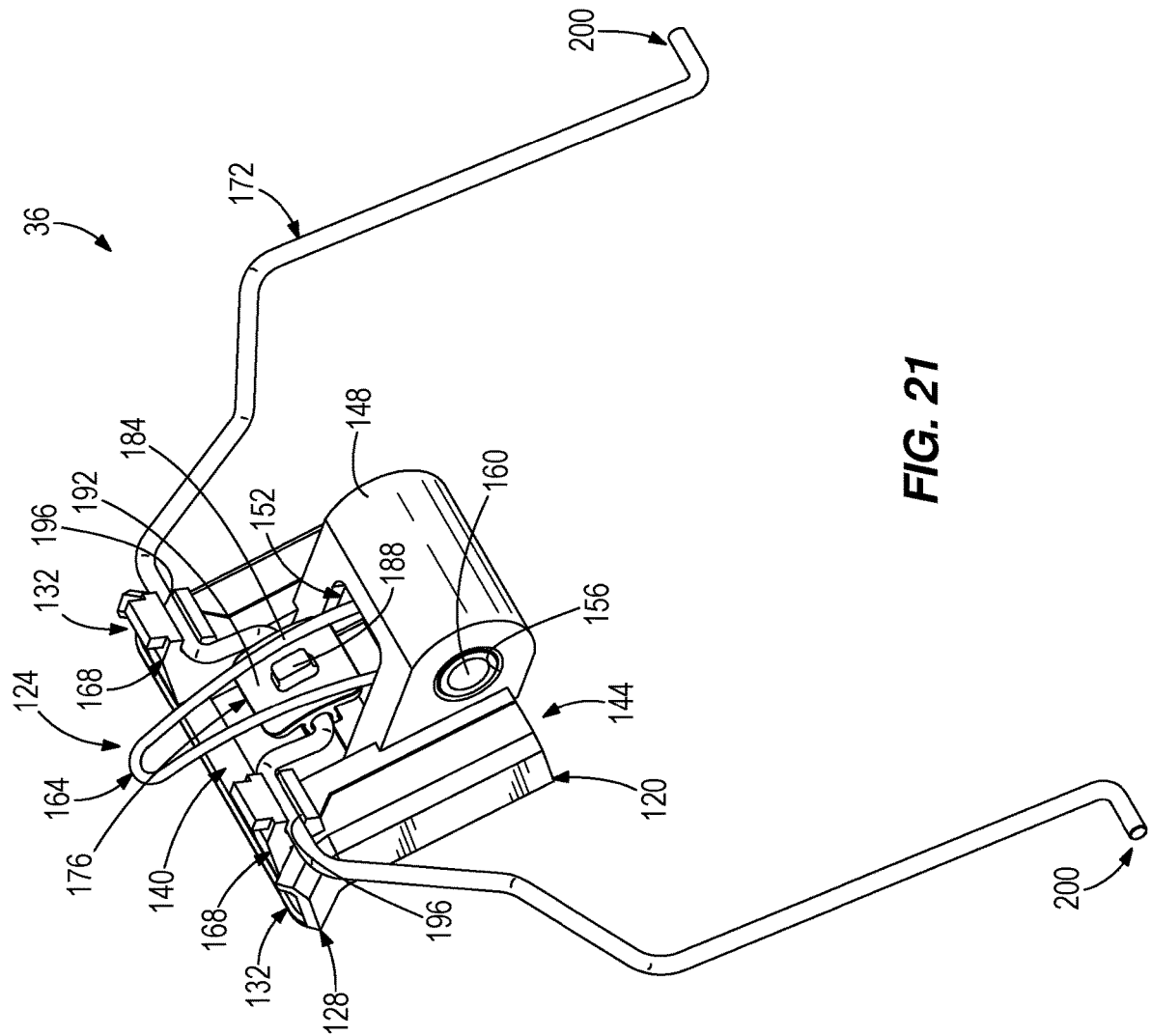
FIG. 21 is a perspective view of one example of an actuator of the protective headwear shown in FIG. 16 with the actuator shown in a first position associated with the first shield being in a downward or operative position, according to one aspect of the present disclosure.
Figure 22:
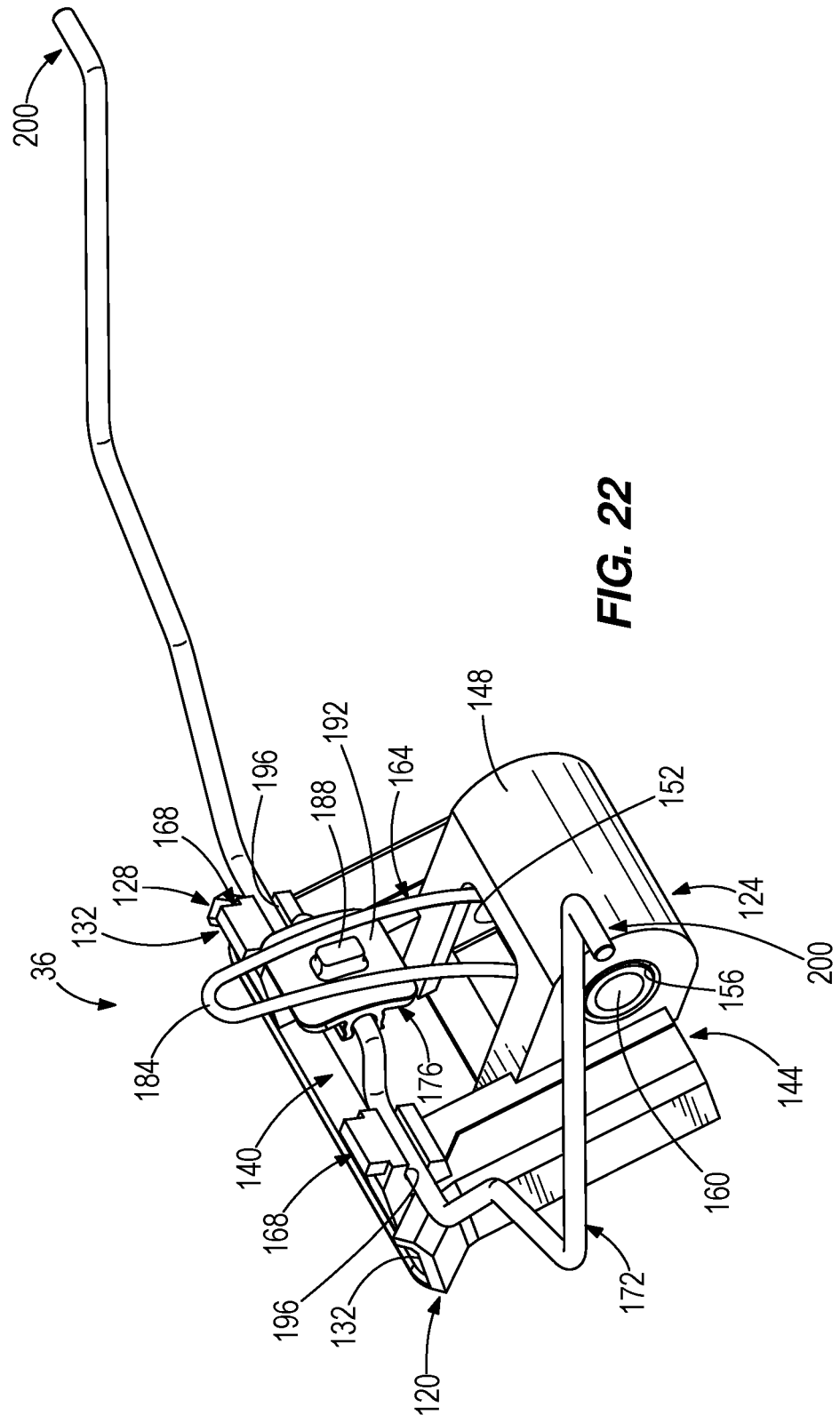
FIG. 22 is a perspective view of the actuator shown in FIG. 21 with the actuator shown in a second position associated with the first shield being in an inoperative, upwardly rotated or intermediate position, according to one aspect of the present disclosure.
Figure 23:
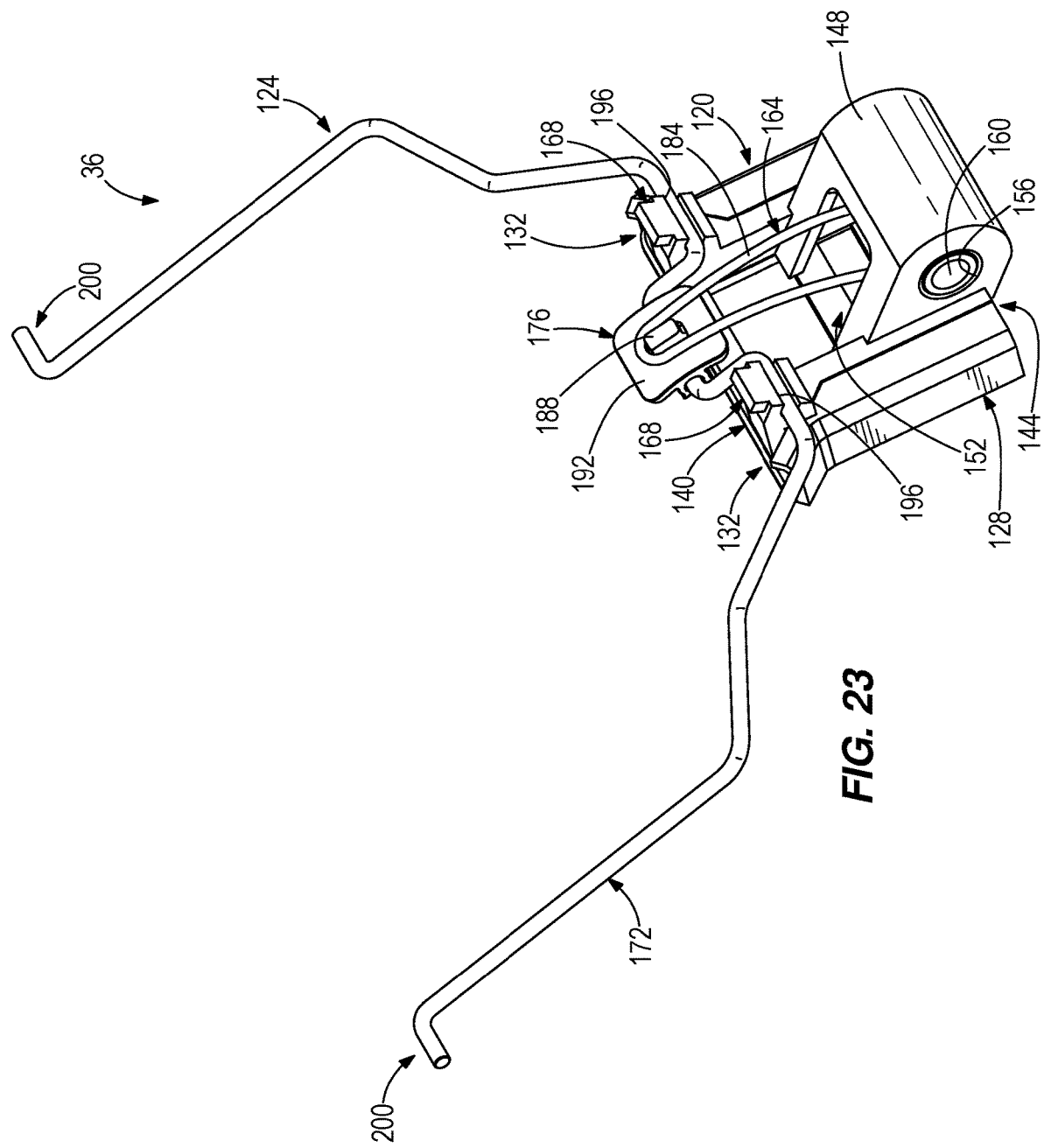
FIG. 23 is a perspective view of the actuator shown in FIG. 21 with the actuator shown in a third position associated with the first shield being in another inoperative or fully upwardly rotated position, according to one aspect of the present disclosure.

With reference to FIG. 20, the biasing member 164 includes a pair of co-axially aligned coils 180 and an engagement portion 184 extending upward from the pair of coils 180. The pin 160 is positioned in the pair of coils 180 and is supported at its ends by the housing 148 via being positioned in the pin openings 156. The engagement portion 184 of the biasing member 164 extends upward out of the housing 148 and engages the engagement member 176. The engagement member 176 includes a projection 188 extending there from that is positioned in a loop formed by the engagement portion 184 of the biasing member 164. The engagement member 176 is coupled to the coupling member 172. The engagement member 176 includes an arcuate front surface 192 that is engageable with the engagement portion 184 of the biasing member 164 which also has an arcuate shape.

Each support arm 168 includes a recess 196 configured to receive a portion of the coupling member 172 to secure the coupling member 172 to the support arms 168. The support arms 168 may be made of a resilient material such that the coupling member 172 is press-fit, friction-fit, interference-fit or otherwise secured within the recesses 196 under friction or compression of the support arms 168 around the coupling member 172. Ends 200 of the coupling member 172 are coupled to an interior of the first shield 28. In one example, the first shield 28 includes a pair of apertures for receiving ends 200 of the coupling member 172. The apertures may be spaced-apart from each other such that the distance between the apertures is less than a distance between the ends 200 of the coupling member 172 at rest. Ends 200 of the coupling member must be pressed toward each other in order to be positioned into the apertures defined in the first shield 28 and release of the ends 200 of the coupling member 172 seat the ends 200 in the apertures. The distance between the apertures does not allow the coupling member 172 to return to its at rest position. Thus, the coupling member 172 is in tension within the apertures, thereby assisting with securement of the coupling member 172 to the first shield 28.

The actuator 36 allows the first shield 28 to rotate relative to the outer shell 24 and be removed from the outer shell 24. With respect to FIG. 21, the actuator 36 is shown in a position corresponding to the first shield 28 being in the fully downward or operative position shown in FIG. 16. In this position, the ends 200 of the coupling member are downward and below the housing 148. The engagement member 176 is also in a downward position along the engagement portion 184 of the biasing member 164. With respect to FIG. 22, the actuator 36 is shown in a position corresponding to the first shield 28 being in a partially rotated upward or intermediate position between the fully downward or operative position shown in FIG. 16 and a fully rotated upward or inoperative position shown in FIG. 17. In this position, the ends 200 of the coupling member 172 are between a fully downward position and a fully upward position, and are generally in line with the housing 148. The engagement member 176 is also in an intermediate position along the engagement portion 184 of the biasing member 164. The arcuate surface 192 of the engagement member 176 rides or slides along the arcuate engagement portion 184 of the biasing member 164 to this intermediate position. With respect to FIG. 23, the actuator 36 is shown in a position corresponding to the first shield 28 being in the fully upward or inoperative position shown in FIG. 17. In this position, the ends 200 of the coupling member 172 are upward and above the housing 148. The engagement member 176 is also in an upward position along the engagement portion 184 of the biasing member 164. The arcuate surface 192 of the engagement member 176 rides or slides along the arcuate engagement portion 184 of the biasing member 164 to this upward position.

Figure 17:
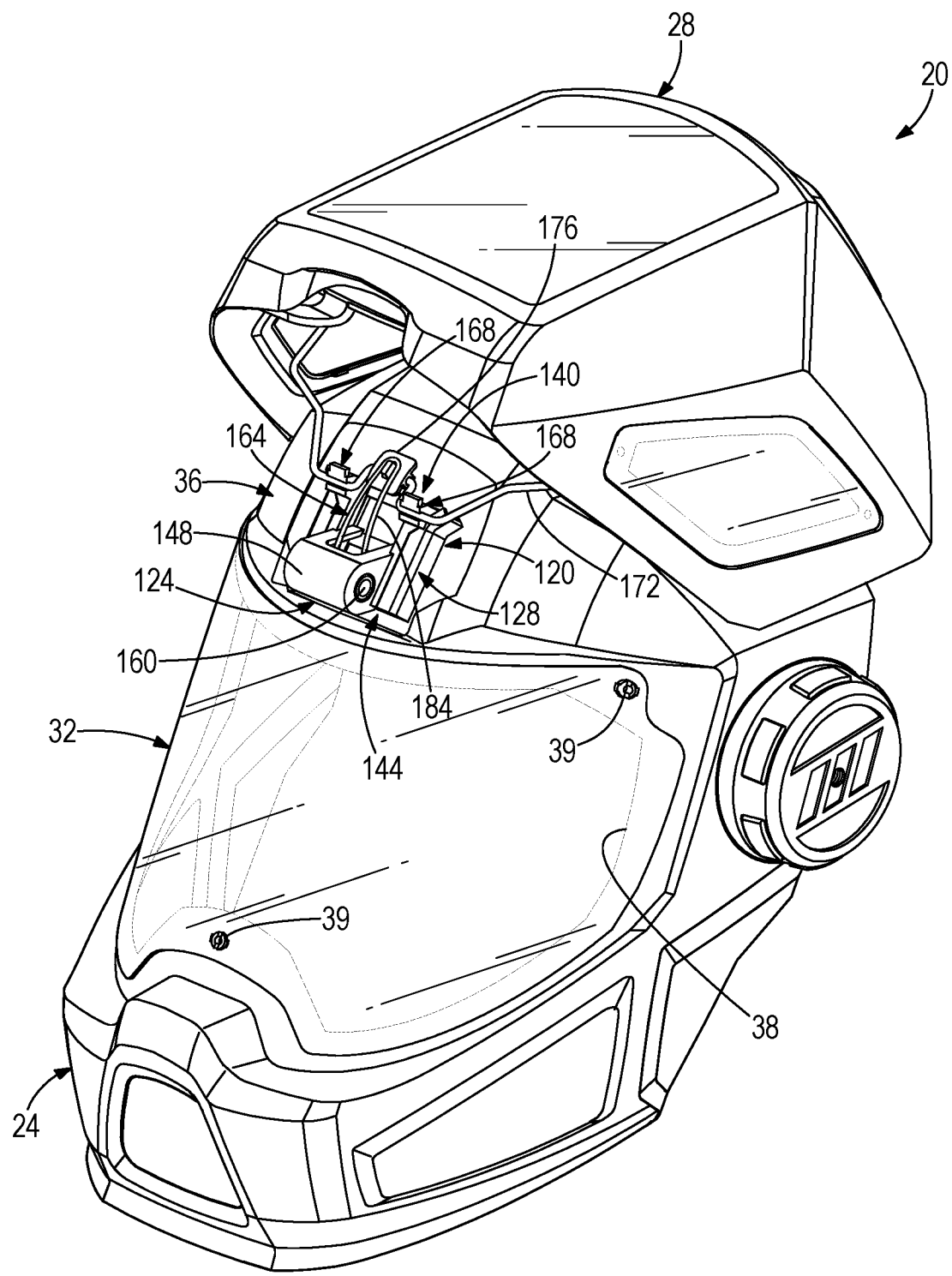
FIG. 17 is a top, front perspective view of the protective headwear shown in FIG. 16 with the first shield in an upwardly rotated or inoperative position, according to one aspect of the present disclosure.
Figure 18:
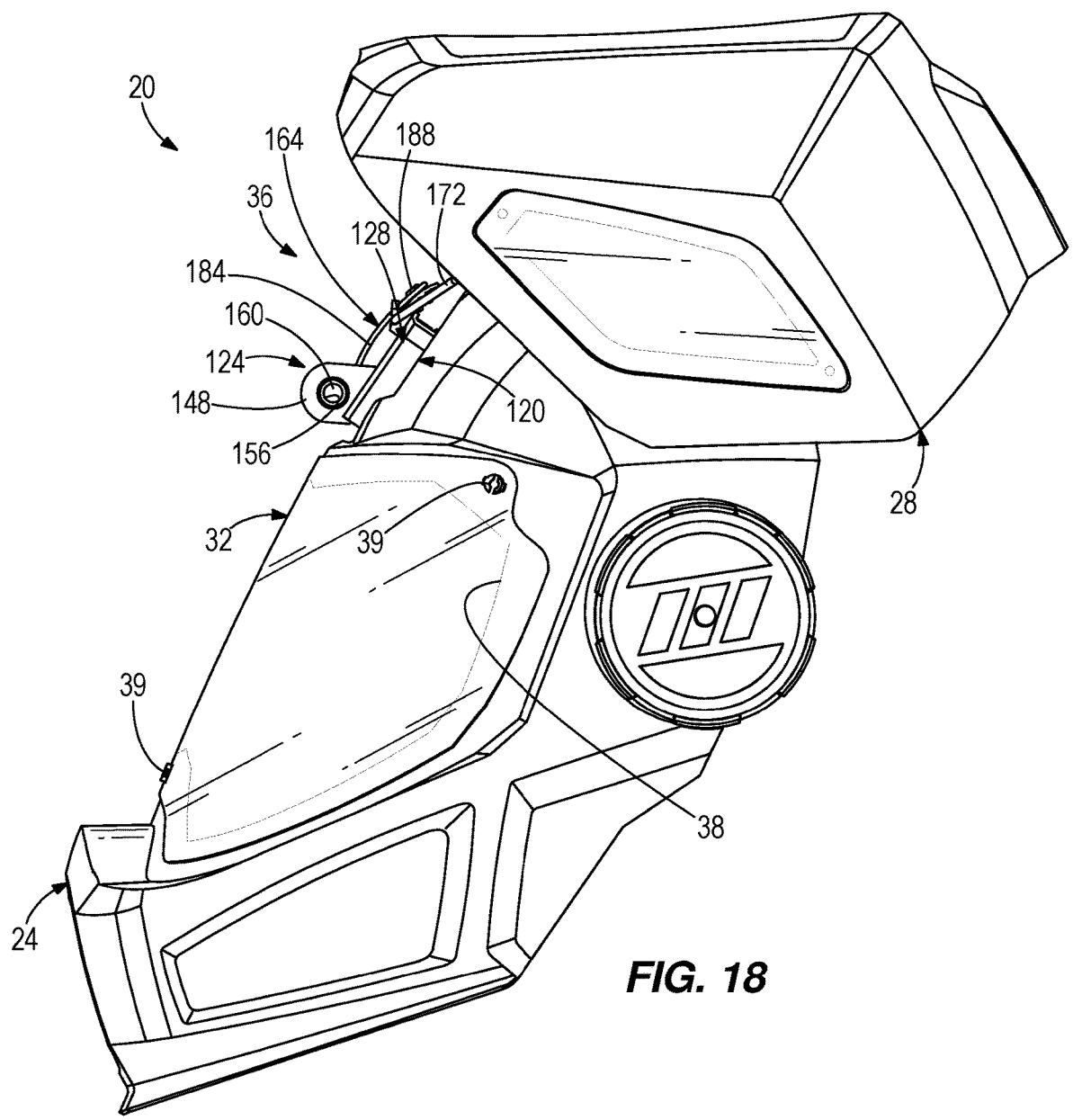
FIG. 18 is a left side view of the protective headwear shown in FIG. 17, according to one aspect of the present disclosure.
Figure 19:
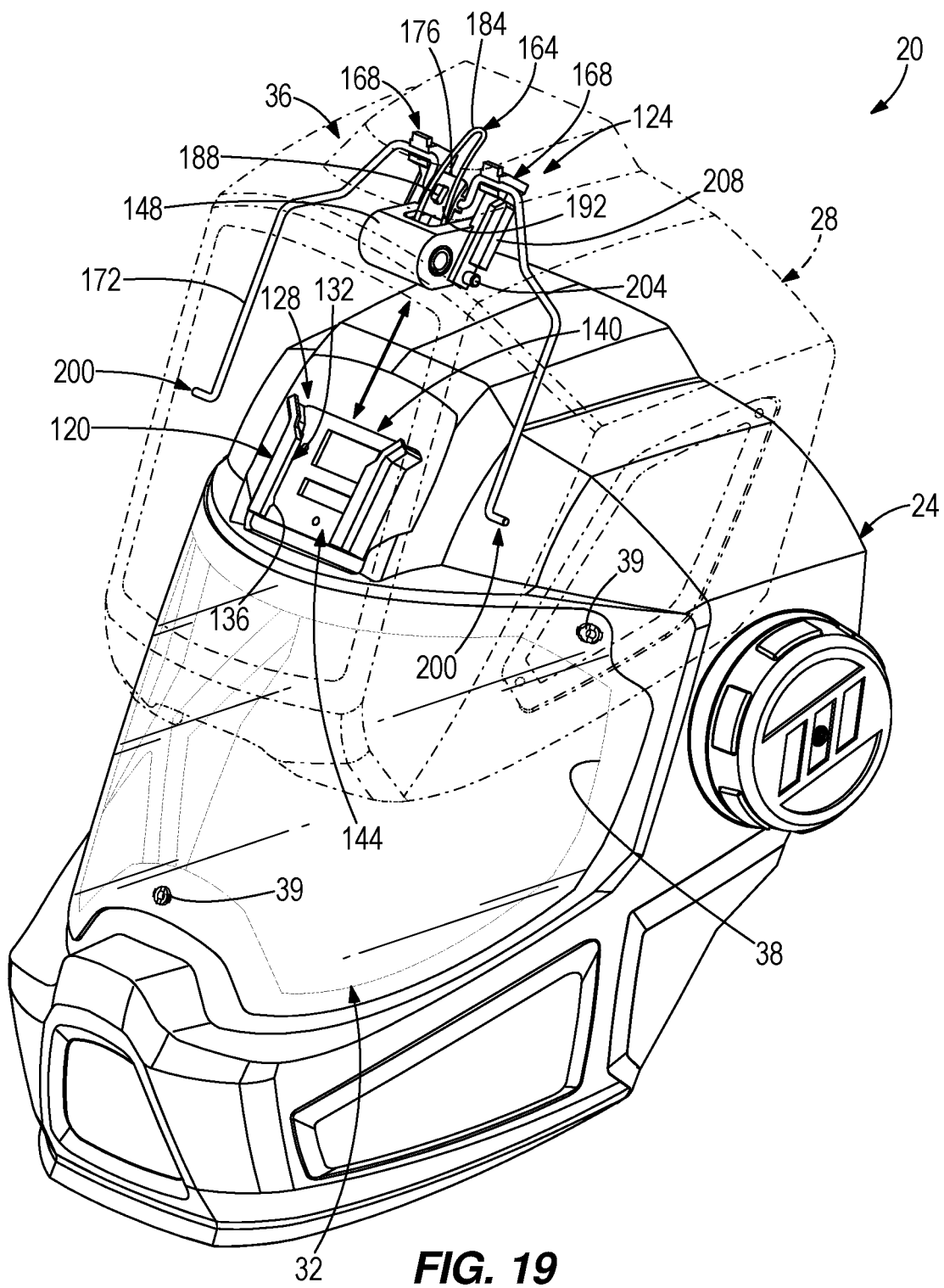
FIG. 19 is a top, front perspective view of the protective headwear shown in FIG. 16 with the first shield shown in another inoperative or removed position, according to one aspect of the present disclosure.

Referring now to FIGS. 17 and 19, the shield portion 124 of the actuator 36 is selectively couplable to the shell portion 120 of the actuator 36. Each support arm 168 includes a projection 204 and a guide member 208 extending there from. The projections 204 and guide members 208 are positionable in respective cavities 132 and are slideable there along between a coupled position (see FIG. 17) and a removed or uncoupled position (see FIG. 19). In the coupled position, the projections 204 are positioned below or behind respective projections 136 defined in the channel cavities 132, which act as catches to retain or secure the shield portion 124 of the actuator 36 to the shell portion 120. To remove the shield portion 124 from the shell portion 120, a wearer may push upward on the housing 148 (if the first shield is in the upward position), or push or pull upward on the first shield 28 (while the first shield is either in the upward position or the downward position) to move the projections 204 on the shield portion 124 past the projections 136 on the shell portion 120. The guide members 208 slide within respective channel cavities 132 to guide the shield portion 124 upward and out of the channel 128. The wider open top end 140 of the channel 128 assists with inserting the projections 204 and guide members 208 back into the channel cavities 132 for recoupling the shield portion 124 to the shell portion 120. To recouple the shield portion 124 to the shell portion 120, the projections 204 on the shield portion 124 are slid downward in the channel cavities 132 until they pass and are below the projections 136 in the channel cavities 132.

The second shields 32 of the variety of examples included in the present disclosure provide a wide viewing angle for wearers of the various examples of protective headwear. The wide viewing angle is due, at least in part, to the large size of the second shield 32 in front of a wearer's eyes. Additionally, the wide viewing angle is due, at least in part, to the continuous or contiguous configuration of the second shield 32 or that the second shield 32 is unitarily formed as one-piece. In one example, the second shield 32 extends from a first side of the outer shell 24 at least in line with a wearer's left eye, across the front of the outer shell 24, and to the second side, opposite the first side, at least in line with the wearer's right eye. In another example, the opposite edges of the second shield 32 are positioned beyond, behind or to a rear of a wearer's eyes. In one example, the second shield 32 comprises at least thirty percent of a front surface area of the outer shell 24. In one example, the second shield 32 comprises between thirty percent and fifty percent of a front surface area of the outer shell 24. In one example, the second shield 32 comprises between thirty percent and seventy-five percent of a front surface area of the outer shell 24. In one example, the second shield 32 comprises between forty percent and sixty percent of a front surface area of the outer shell 24. In one example, the second shield 32 comprises between forty percent and fifty percent of a front surface area of the outer shell 24. In one example, the second shield 32 comprises at least fifty percent of a front surface area of the outer shell 24. In one example, the second shield 32 comprises at least sixty percent of a front surface area of the outer shell 24. In one example, the second shield 32 comprises at least seventy-five percent of a front surface area of the outer shell 24. It should be understood that the second shield 32 may comprise any percentage of a front surface area of the outer shell 24 and all of such possibilities are intended to be within the spirit and scope of the present disclosure.

It should be understood that the features of the present disclosure may be incorporated into different types of protective headwear. The combination of the features of the present disclosure and any type of protective headwear are intended to be within the spirit and scope of the present disclosure.

It should be understood that the use of any orientation or directional terms herein such as, for example, "top", "bottom", "front", "rear", "back", "left", "right", "side", etc., is not intended to imply only a single orientation of the item with which it is associated or to limit the present disclosure in any manner. The use of such orientation or directional terms is intended to assist with the understanding of principles disclosed herein and to correspond to the exemplary orientation illustrated in the drawings. For example, the protective headwear may be utilized in any orientation and use of such terms is intended to correspond to the exemplary orientation of the protective headwear illustrated in the drawings. The use of these terms in association with the protective headwear is not intended to limit the protective headwear to a single orientation or to limit the protective headwear in any manner.

The Abstract of the disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments of the disclosure have been described, it will be apparent to those of ordinary skill in the art that other embodiments and implementations are possible within the scope of the disclosure. Accordingly, the disclosure is not to be restricted except in light of the attached claims and their equivalents.

The invention claimed is:

1. A protective headwear comprising:
   an outer shell including a front, a right side, a left side opposite the right side, a top and a bottom opposite the top;
   a first shield coupled to the outer shell and rotatable between a first position and a second position, wherein the first shield is selectively removable from the outer shell;
   a second shield coupled to the outer shell, wherein the first shield covers the second shield to a greater extent in the first position than in the second position, and wherein the first shield is positioned over the top of the outer shell in the second position; and
   a first actuator including a shell portion coupled to the outer shell and a shield portion coupled to the first shield, wherein the shell portion and the shield portion are selectively engageable to couple the first shield to the outer shell, and wherein the first actuator is configured to be actuated to a first actuator position to allow removal of the first shield from the outer shell, and wherein, with the first shield removed from the outer shell, the shell portion remains coupled to the outer shell and the shield portion remains coupled to the first shield; and a second actuator, wherein the second actuator is configured to be actuated to a second actuator position to facilitate rotation of the first shield relative to the outer shell.

2. The protective headwear of claim 1, wherein the first shield completely covers the second shield in the first position and wherein the first shield exposes at least a portion of the second shield in the second position.

3. The protective headwear of claim 1, wherein the first shield has a first viewing capacity and the second shield has a second viewing capacity greater than the first viewing capacity.

4. The protective headwear of claim 1, wherein the outer shell includes a rear opposite the front, wherein the first shield is coupled to the front of the outer shell and is removed from the outer shell by moving the first shield in a direction out from the front of the outer shell along an axis extending from the rear toward the front of the outer shell.

5. The protective headwear of claim 1, wherein the first shield rotates relative to the outer shell about a first axis, and wherein the first shield is removed from the outer shell along a second axis transverse to the first axis.

6. The protective headwear of claim 1, wherein the first shield rotates relative to the outer shell about a first axis, and wherein the first shield is removed from the outer shell along a second axis perpendicular to the first axis.

7. The protective headwear of claim 1, wherein the first shield does not cover the second shield with the first shield in the second position such that viewing through the second shield is unimpeded.

8. The protective headwear of claim 1, further comprising a biasing member coupled to the first shield, wherein the biasing member is configured to bias the first shield toward the second position.

9. The protective headwear of claim 8, wherein the biasing member cooperates with the first shield as an over-center biasing member and is configured to selectively bias the first shield toward either the first position or the second position based on a position of the first shield.

10. The protective headwear of claim 1, wherein the first shield has an inner surface and an outer surface, wherein the inner surface of the first shield faces the second shield with the first shield in the first position and faces the top of the shell with the first shield in the second position.

11. The protective headwear of claim 1, wherein the first actuator position comprises the actuator being actuated in a first amount, and the second actuator position comprises the actuator being actuated in a second amount.

12. The protective headwear of claim 1, wherein the second actuator is configured to be actuated to the second actuator position to allow rotation of the first shield relative to the outer shell.

13. The protective headwear of claim 1, wherein the first shield is an auto-darkening shield.

14. The protective headwear of claim 1, further comprising a biasing member coupled to the first shield, wherein the biasing member is configured to bias the first shield towards the second position.

15. A protective headwear comprising:

an outer shell including a front, a right side, a left side opposite the right side, a top and a bottom opposite the top;

a first shield coupled to the outer shell and rotatable between a first position and a second position, wherein the first shield is selectively removable from the outer shell;

a second shield coupled to the outer shell, wherein the first shield covers the second shield to a greater extent in the first position than in the second position, and wherein the first shield is positioned over the top of the outer shell in the second position; and a first actuator including a shell portion coupled to the outer shell and a shield portion coupled to the first shield, wherein the shell portion and the shield portion are selectively engageable to couple the first shield to the outer shell, and wherein the actuator is configured to be actuated to a first actuator position to allow removal of the first shield from the outer shell, and wherein, with the first shield removed from the outer shell, the shell portion remains coupled to the outer shell and the shield portion remains coupled to the first shield; and a second actuator, wherein the second actuator is configured to be actuated to a second actuator position to facilitate rotation of the first shield relative to the outer shell.

16. The protective headwear of claim 15, wherein the second actuator is configured to move relative to the first shield when actuated.

17. The protective headwear of claim 15, wherein the first and second actuator each comprise at least one of a detent type actuator, a spring biased actuator, a projection and recess actuator, a ratchet type actuator, a latch actuator, a latch buckle actuator, or a friction-based actuator.

18. The protective headwear of claim 15, wherein the second actuator is configured to be actuated to the second actuator position to allow rotation of the first shield relative to the outer shell.

19. The protective headwear of claim 15, further comprising a biasing member coupled to the first shield, wherein the biasing member is configured to bias the first shield towards the second position.

20. The protective headwear of claim 15, wherein the first shield is an auto-darkening shield.

21. The protective headwear of claim 15, further comprising a biasing member coupled to the first shield, wherein the biasing member is configured to bias the first shield towards the second position, wherein the second actuator is configured to move relative to the first shield when actuated.

* * * * *